United States Patent
Takahashi et al.

[19]

[11] Patent Number: 5,877,802
[45] Date of Patent: Mar. 2, 1999

[54] VIDEO-SIGNAL PROCESSING DEVICE CONNECTABLE TO AN ELECTRONIC ENDOSCOPE

[75] Inventors: Akihiro Takahashi; Kouhei Iketani, both of Tokyo, Japan

[73] Assignee: Asahi Kogaku Kogyo Kabushiki Kaisha, Tokyo, Japan

[21] Appl. No.: 845,191

[22] Filed: Apr. 21, 1997

[30] Foreign Application Priority Data

May 21, 1996 [JP] Japan .................................. 8-149917

[51] Int. Cl.⁶ ............................. A61B 1/04; H04N 7/18
[52] U.S. Cl. ............................. 348/71; 128/908; 348/74; 348/589; 348/600; 600/134
[58] Field of Search .................... 348/65, 71, 74, 348/589, 600; 128/908; 600/134; H04N 7/18

[56] References Cited

U.S. PATENT DOCUMENTS

| | | | |
|---|---|---|---|
| 4,045,815 | 8/1977 | Griffith | 348/589 |
| 4,654,701 | 3/1987 | Yabe | 348/589 |
| 4,712,133 | 12/1987 | Kikuchi | 348/589 |
| 4,727,417 | 2/1988 | Kanno | 348/589 |
| 4,727,418 | 2/1988 | Kato | 348/589 |
| 4,819,065 | 4/1989 | Eino | 348/589 |
| 4,841,363 | 6/1989 | Ams | 348/589 |
| 4,853,772 | 8/1989 | Kikuchi | 348/71 |
| 5,543,831 | 8/1996 | Tsuji | 348/65 |
| 5,739,868 | 4/1998 | Butler | 348/600 |

*Primary Examiner*—Howard Britton
*Attorney, Agent, or Firm*—Greenblum & Bernstein, P.L.C.

[57] ABSTRACT

A video-signal processing device is connectable to an electronic endoscope designed to output at least one kind of video signal, and comprises a character-information signal producer for producing a character-information signal on the basis of character-code data, and an adder for adding the character-information signal to the video signal outputted from the electronic endoscope, whereby the video signal carrying the character-information signal is fed outside from the device. When the endoscope further outputs a control signal in response to a turning-ON of a function switch thereof, the device comprises a memory for storing fixed character-code data; and a memory-reader for reading the fixed character-code data from the memory in response to the control signal outputted from the endoscope. The character-information signal producer produces a fixed character-information signal on the basis of the fixed character-code data read from the memory.

56 Claims, 18 Drawing Sheets

VIDEO-SIGNAL PROCESSING DEVICE CONNECTABLE TO AN ELECTRONIC ENDOSCOPE

BACKGROUND OF THE INVENTION

1. Field of the Invention

The present invention relates to a video-signal processing device connectable to an electronic endoscope, and more particularly relates to a video-signal processing device that intervenes between an electronic endoscope and peripheral equipment such as a television (TV) monitor, a video tape recorder, a printer, a video-image processing computer, and so on.

2. Description of the Related Art

The described electronic endoscope comprises a flexible conduit and a video processor to which the flexible conduit is detachably joined.

The flexible conduit has an objective lens system provided at the distal end thereof, and a solid state image sensor such as a CCD (charge-coupled device) associated therewith. An object to be photographed is focused by the objective lens system, as an optical image, on a light receiving surface of the CCD image sensor. The optical image is converted into analog image-pixel signals by the CCD image sensor, and the analog image-pixel signals are successively read out of the image sensor by a CCD driver circuit.

Also, the flexible conduit has an optical guide provided therewithin, and the optical guide terminates at a light-emitting end face of the distal end of the flexible conduit. The video processor includes an optical guide provided therein. When the flexible conduit is joined to the video processor, one end of the optical guide of the video processor is connected to a proximal (base) end of the optical guide of the flexible conduit.

The video processor of the electronic endoscope also has a light source, and a collective lens system associated therewith. Light rays emitted from the light source are focused on the other end face of the optical guide of the video processor by the collective lens system. Thus, the front area of the distal end of the flexible conduit is illuminated by the light rays emitted from the light-emitting end face of the optical guide of the flexible conduit.

For reproduction of a photographed image as a color image, for example, an RGB field sequential type color imaging system is introduced in the electronic endoscope. Namely, a rotary RGB color filter is placed in a position intervening between the light source and the inner end face of the optical guide of the video processor, and the RGB color filter is rotated at a given frequency of rotation. An object to be photographed is thereby sequentially illuminated by red light rays, green light rays, and blue light rays. Thus, a red optical image, a green optical image, and a blue optical image are focused on the light receiving surface of the CCD image sensor at given time intervals.

Analog color-image-pixel signals successively read from the CCD image sensor by the CCD driver circuit are fed to the video processor, which processes the analog color-image pixel signals to thereby produce a color video signal. Usually, the video processor of the electronic endoscope is connected to a medical TV monitor designed to ensure electrical security, and a photographed image is reproduced on the medical TV monitor on the basis of the color video signal fed from the video processor. In this context, "electrical security" designates both confidentiality and protecting a patient from stray current on the signal line.

Also, the electronic endoscope may be connected to a consumer TV monitor at medical site for reproduction of a photographed image thereon. However, in general, a consumer TV monitor is not designed to ensure electrical security.

On the other hand, a user may want to connect an electronic endoscope to other peripheral equipment (such as a video tape recorder, a printer, an image-processing computer and so on) other than a TV monitor. To this end, the video processor of the electronic endoscope is arranged to output at least two kinds of color video signals. However, in this case, of course, the peripheral equipment are not designed to ensure electrical security.

Further, the user may wish to connect the electronic endoscope to a peripheral remotely located from where the electronic endoscope is used. For example, at a large hospital of more than two buildings, there may be a case where a color video signal must be fed from the electronic endoscope used in a room of a first building to a peripheral location in a room of another building. In this case, the video signal is preferably fed as a digital video signal from the electronic endoscope to the peripheral equipment, because an analog video signal is susceptible to attenuation.

Nevertheless, the feeding of the digital video signal to the remote peripheral equipment is not expedient, because an expensive (parallel) signal cable having a plurality of signal lines, corresponding to a bit number of the digital video signal, must be laid therebetween.

Furthermore, when a photographed image is reproduced on a peripheral such as a television (TV) monitor, a video tape recorder, a printer, an image-processing computer, and so on, the user may wish to add messages or comments concerning the reproduced image thereto.

SUMMARY OF THE INVENTION

Therefore, a main object of the present invention is to provide a video-signal processing device connectable to an electronic endoscope such that at least one kind of video signal is fed from the electronic endoscope to a peripheral for reproducing an image on the basis of the video signal, wherein character-information signals can be added to the video signal so that messages or comments based upon the character-information signals are reproduced together with the video image.

Another object of the present invention is to provide a video-signal processing device of the above-mentioned type, arranged such that at least one kind of video signal is fed as a serial digital signal to a peripheral, whereby the feeding of the video signal to the peripheral is possible without an expensive (parallel) signal cable having a plurality of signal lines.

Yet another object of the present invention is to provide a video-signal processing device of the above-mentioned type, wherein the feeding of an uncontrollable image in the video signal to the peripheral can be prevented during the connection of the video-signal processing device to the electronic endoscope.

Still yet another object of the present invention is to provide a video-signal processing device of the above-mentioned type, wherein the feeding of images in the video signal to the peripheral equipment can be forcibly stopped, if necessary.

Still yet another object of the present invention is to provide a video-signal processing device of the above-mentioned type, wherein the feeding of an image in the video signal to the peripheral equipment is performed such that the electronic endoscope is electrically isolated from the video-signal processing for electrical security.

In accordance with one aspect of the present invention, there is provided a video-signal processing device connectable to an electronic endoscope designed to output at least one kind of video signal, the device comprising: a character-information signal producer for producing a character-information signal on the basis of character-code data; and an adder for adding the character-information signal to the video signal outputted from the electronic endoscope, whereby the video signal carrying the character-information signal is fed from the device.

Preferably, the video-signal processing device further comprises a manual input device for inputting character-code data to the character-information signal producer, whereby a variable optional character-information signal is produced by the character-information signal producer. The manual input device may comprise a keyboard.

Also, preferably, a video-signal processing device further comprises an isolation coupler for inputting the video signal from the electronic endoscope to the device, and electrically isolating the electronic endoscope from the device. The isolation coupler may be a photo-coupler or a transformer coupler.

In accordance with another aspect of the present invention, there is provided a video-signal processing device connectable to an electronic endoscope designed to output at least one kind of video signal, the electronic endoscope further outputting a control signal in response to a turning-ON of a function switch thereof, the device comprising: a memory for storing fixed character-code data; a memory-reader for reading the fixed character-code data from the memory in response to the control signal outputted from the electronic endoscope; a character-information signal producer for producing a fixed character-information signal on the basis of the fixed character-code data read from the memory; and an adder for adding the character-information signal to the video signal outputted from the electronic endoscope, whereby the video signal carrying the character-information signal is fed outside from the device.

Preferably, the video-signal processing device according to the second aspect of the present invention further comprises a manual inputter for inputting variable optional character-code data to the character-information signal producer, whereby a variable optional character-information signal is produced by the character-information signal producer. The manual inputter may comprise a keyboard.

Also, preferably, the video-signal processing device further comprises respective isolation couplers for inputting the video signal and the control signal from the electronic endoscope to the device and electrically isolating the electronic endoscope from the device. Each of the isolation couplers may be a photo-coupler or a transformer coupler.

In accordance with yet another aspect of the present invention, there is provided a video-signal processing device connectable to an electronic endoscope designed to output at least one kind of electric analog video signal, the device comprising: a character-information signal producer for producing a character-information signal on the basis of character-code data; an adder for adding the character-information signal to the electric analog video signal outputted from the electronic endoscope; an analog-to-digital converter for converting the electric analog video signal carrying the character-information signal into a parallel electric digital video signal; and a parallel-to-serial converter for converting the parallel electric digital video signal into a serial electric digital video signal, whereby the electric analog video signal outputted from the electronic endoscope and carrying the character-information signal is fed from the device as the serial electric digital video signal.

In accordance with still yet another aspect of the present invention, there is provided a video-signal processing device connectable to an electronic endoscope designed to output at least one kind of electric analog video signal, the electronic endoscope further outputting a control signal in response to a turning-ON of a function switch thereof, the device comprising: a memory for storing fixed character-code data; a memory-reader for reading the fixed character-code data from the memory in response to the control signal outputted from the electronic endoscope; a character-information signal producer for producing a fixed character-information signal on the basis of the fixed character-code data read from the memory; and an adder for adding the character-information signal to the electric analog video signal outputted from the electronic endoscope; and analog-to-digital converter for converting the electric analog video signal carrying the character-information signal into a parallel electric digital video signal; and a parallel-to-serial converter for converting the parallel electric digital video signal into a serial electric digital video signal, whereby the electric analog video signal outputted from the electronic endoscope and carrying the character-information signal is fed outside from the device as the serial electric digital video signal.

In accordance with still yet another aspect of the present invention, there is provided a video-signal processing device connectable to an electronic endoscope designed to output a component-type electric analog color video signal as at least one kind of video signal, the component-type electric analog color video signal being composed of a composite synchronizing signal-component, and at least three kinds of video signal-components, the device comprising: a character-information signal producer for producing a character-information signal on the basis of character-code data; an adder for adding the character-information signal to the video signal-components; an analog-to-digital converter to converting each of the respective video signal-components carrying the character-information signals into a parallel electric digital video signal-components; a parallel-to-serial converter for converting the respective parallel digital video signal-components into serial digital video-signal-components and for outputting the serial digital video-signal-components in accordance with a series of clock pulses; and a phase-locked loop circuit for coinciding a phase of the series of clock pulses with a phase of the composite synchronizing signal component of the component-type electric analog color video signal, whereby the serial digital video signal-components are outputted outside at proper timing from the device.

In accordance with still yet another aspect of the present invention, there is provided a video-signal processing device connectable to an electronic endoscope designed to output a component-type electric analog color video signal as at least one kind of video signal, the component-type electric analog color video signal being composed of a composite synchronizing signal-component, and at least three kinds of video signal-components, the electronic endoscope further outputting a control signal in response to a turning-ON of a function switch thereof, the device comprising: memory for storing fixed character-code data; a memory-reader for reading the fixed character-code data from the memory in response to the control signal outputted from the electronic endoscope; a character-information signal producer for producing a fixed character-information signal on the basis of the fixed character-code data read from the memory; an adder for adding the character-information signal to the video signal-component; an analog-to-digital converter for converting each of the respective video signal-components carrying the character-information signals into a parallel electric digital video signal-components; a parallel-to-serial converter for converting the respective parallel digital video signal-components into serial digital video-signal-components and for outputting the serial digital video-signal-components in accordance with a series of clock pulses; and a phase-locked loop circuit for coinciding a phase of the series of clock pulses with a phase of the composite synchronizing signal component of the component-type electric analog color video signal, whereby the serial digital video signal-components are outputted outside at proper timing from the device.

The video-signal processing device having the phase-locked loop circuit may further comprise: a phase-lock detector for detecting the coincidence of the phase of the series of clock pulses with the phase of the composite synchronizing signal; a signal-output stopper for stopping the outputting of the serial digital video-signal-components from the device until the phase-lock detector detects the coincidence of the phase of the series of clock pulses with the phase of the composite synchronizing signal; and a display for displaying a message announcing that the coincidence of the phase of the series of clock pulses with the phase of the composite synchronizing signal of the component-type electric analog color video signal is detected by the phase-lock detector.

In accordance with still yet another aspect of the present invention, there is provided a video-signal processing device connectable to an electronic endoscope designed to output a component-type electric analog color video signal as at least one kind of video signal, the component-type electric analog color video signal being composed of a composite synchronizing signal-component, and three kinds of video-signal-components, the device comprising: a synchronizing-signal detector for an inputting composite synchronizing signal to the device; a signal-output stopper for stopping an outputting of the three kinds of video-signal-components outside from the device until the synchronizing-signal detector detects the inputting of the composite synchronizing signal to the device. Preferably, this device further comprises a displayer for displaying a message announcing that the synchronizing-signal detector detects the inputting of the composite synchronizing signal to the device.

In accordance with still yet another aspect of the present invention, there is provided a video-signal processing device connectable to an electronic endoscope designed to output a component-type electric analog color video signal as at least one kind of video signal, the component-type electric analog color video signal being composed of a composite synchronizing signal-component, and three kinds of video-signal-components, the device comprising: a converter/outputter for converting the three kinds of video-signal-components into serial digital video-signal-components and for outputting the serial digital video-signal-components outside from the device in accordance with a series of clock pulses; a phase-locked loop circuit for coinciding a phase of the series of clock pulses with a phase of the composite synchronizing signal component of the component-type electric analog color video signal, a phase-lock detector for detecting the coincidence of the phase of the series of clock pulses with the phase of the composite synchronizing signal; and a signal-output stopper for stopping the outputting of the serial digital video-signal-components from the device until the phase-lock detector detects the coincidence of the phase of the series of clock pulses with the phase of the composite synchronizing signal. Preferably, the device further comprises a displayer for displaying a message announcing that the coincidence of the phase of the series of clock pulses with the phase of the composite synchronizing signal of the component-type electric analog color video signal is detected by the phase-lock detector.

In accordance with still yet another aspect of the present invention, there is provided a video-signal processing device connectable to an electronic endoscope designed to output at least two kinds of video signals, the device comprising: a switch circuit provided in output-signal lines for the two kinds of video signals; a first manual switch for operating the switch circuit in such a manner that an outputting of one of the two kind of video signals from the device is forcibly stopped when turning ON the first manual switch; a first indicator associated with the first manual switch for indicating the turned-ON of the first manual switch; a second manual switch for operating the switch circuit in such a manner that an outputting of the other kind of video signals from the device is forcibly stopped when turning ON the second manual switch; and a second indicator associated with the second manual switch for indicating the turned-ON of the second manual switch.

BRIEF DESCRIPTION OF THE DRAWINGS

The objects and other objects of the present invention will be better understood from the following description, with reference to the accompanying drawings in which.

DESCRIPTION OF THE PREFERRED EMBODIMENTS

Figure 1:
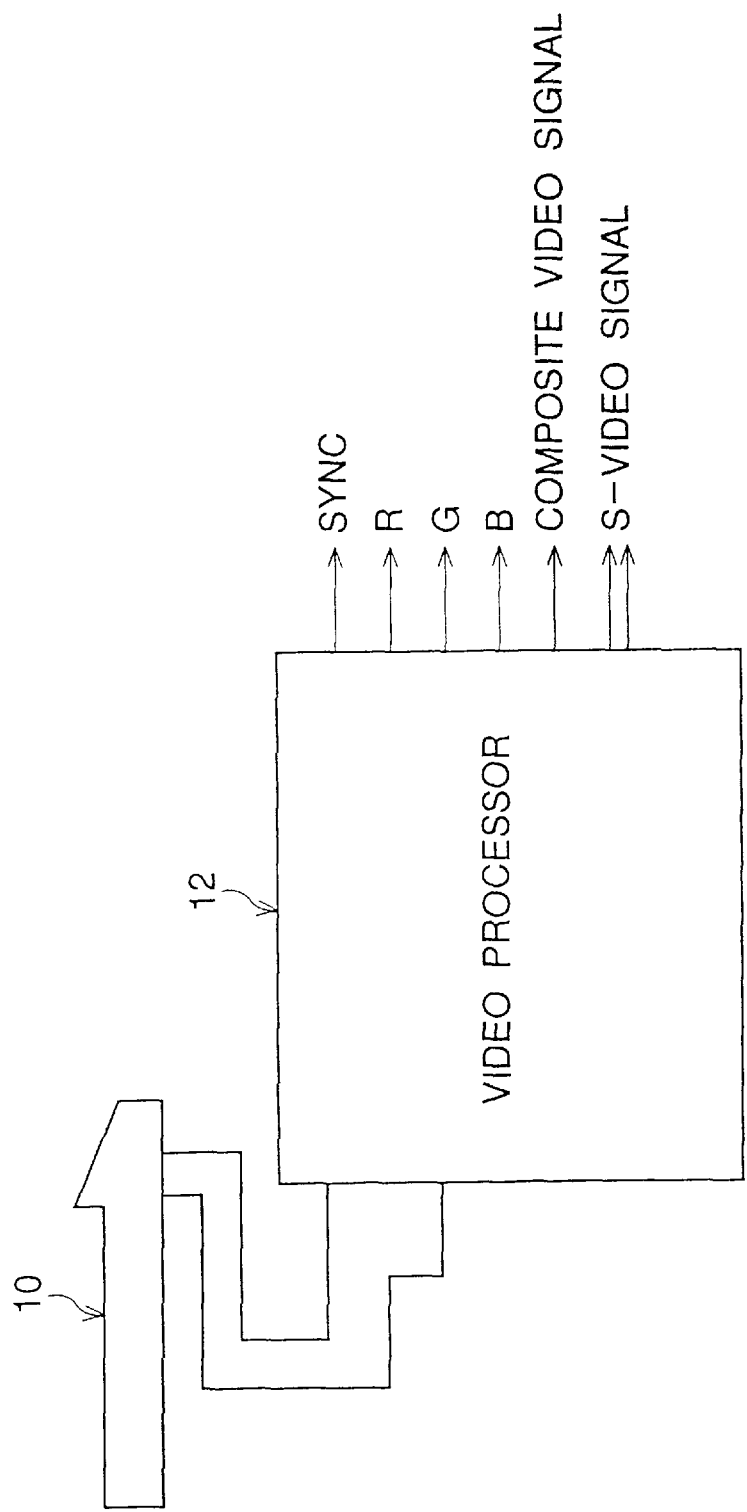
FIG. 1 is a schematic view showing an electronic endoscope to which a video-signal processing device according to the present invention may be connected.

FIG. 1 schematically shows an electronic endoscope, to which a video-signal processing device according to the present invention may be connected. The electronic endoscope comprises a flexible conduit 10, and a video processor 12 to which the flexible conduit 10 is detachably joined.

The flexible conduit 10 has an objective lens system (not shown) provided at the distal end thereof, and a solid state image sensor such as a CCD (charge-coupled device, not shown) associated therewith. An object to be photographed is focused as an optical image on a light receiving surface of the CCD image sensor by the objective lens system. The optical image is converted into analog image-pixel signals by the CCD image sensor, and the analog image-pixel signals are successively read out of the image sensor by a CCD driver circuit therefor.

Also, the flexible conduit 10 has an optical guide provided therewithin, and the optical guide may be formed by a bundle of optical fibers. The optical guide terminates at a light-emitting end face at the distal end of the flexible conduit 10. On the other hand, the video processor 12 includes an optical guide (not shown) provided therein, and this optical guide may be also formed by a bundle of optical fibers. When the flexible conduit 10 is joined to the video processor 12, one end of the optical guide of the video processor 12 is connected to a proximal end of the optical guide of the flexible conduit 10.

The video processor 12 also has a light source (not shown), and a collective lens system (not shown) associated therewith, and light rays emitted from the light source are focused on the other end face of the optical guide of the video processor 12 by the collective lens system. Thus, a front area of the distal end of the flexible conduit 10 is illuminated by the light rays emitted from the light-emitting end face of the optical guide of the flexible conduit 10.

To reproduce a photographed image as a color image, for example, an RGB field sequential type color imaging system is introduced in the electronic endoscope. That is, a rotary RGB color filter is intervened between the light source and the inner end face of the optical guide of the video processor 12, and the RGB color filter is rotated at a given frequency of rotation. An object to be photographed is therefore sequentially illuminated by red light rays, green light rays, and blue light rays. Thus, a red optical image, a green optical image, and a blue optical image are focused on the light receiving surface of the CCD image sensor at given time intervals.

Analog color-image-pixel signals successively read from the CCD image sensor are fed to the video processor 12, and are then subjected to various image-processing such as white-balance processing, gamma-correction processing and so on. In the electronic endoscope shown in FIG. 1, three kinds of color video signals are produced on the basis of the processed color-image-pixel signals, and are outputted from the video processor 12.

Namely, as shown in FIG. 1, as a first kind of color video signal, a component-type color video signal composed of a composite synchronizing signal (SYNC), a red video signal (R), a green video signal (G), and a blue video signal (B) is output from the video processor 12; as a second kind of color video signal, an S-video signal composed of a luminance signal and an amplitude-modulated (AM) color-difference signal is output from the video processor 12; and, as a third kind of color video signal, a composite color video signal combined with a luminance signal and an amplitude-modulated (AM) color-difference signal is output from the video processor 12.

Figure 2:
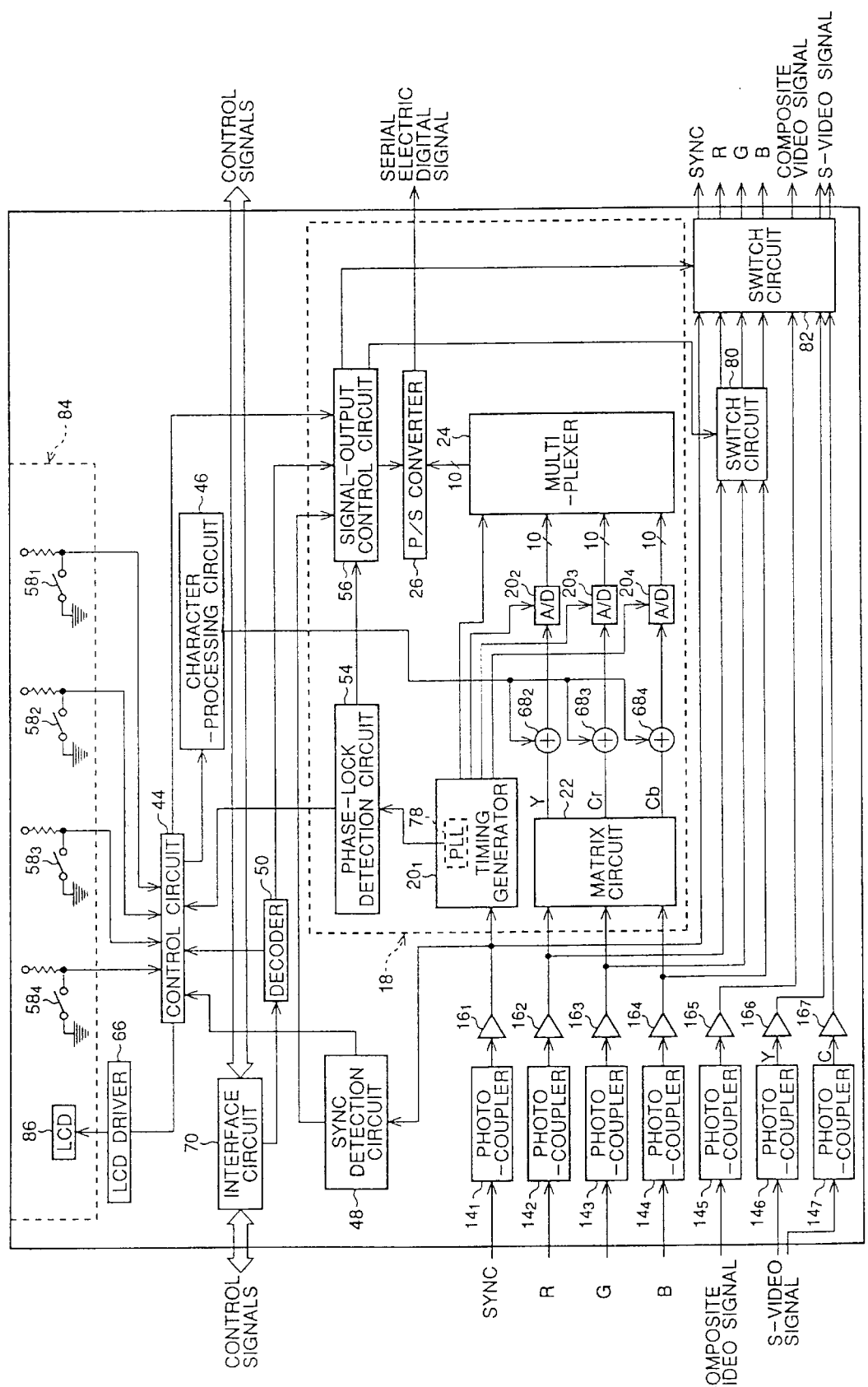
FIG. 2 is a block diagram showing a first embodiment of the video-signal processing device according to the present invention.

FIG. 2 shows a block diagram of a first embodiment of the video-signal processing device according to the present invention, which is connectable to the video processor 12 of the electronic endoscope shown in FIG. 1. The video-signal processing device comprises seven photo-couplers $14_1$ to $14_7$, and, when the video-signal processing device is connected to the video processor 12, the three kinds of video signals output from the video processor 12 are input to the seven photo-couplers $14_1$ to $14_7$.

In particular, the respective composite synchronizing signal (SYNC), red video signal (R), green video signal (G), and blue video signal (B) of the first kind of color video signal (the component-type color video signal) are input to the photo-couplers $14_1$ to $14_4$; the respective luminance signal and amplitude-modulated (AM) color-difference signal of the second kind of color video signal (the S-video signal) are input to the photo-couplers $14_6$ and $14_7$; and the third kind of color video signal, i.e., the composite color video signal combined with the luminance signal and the amplitude-modulated (AM) color-difference signal is input to the photo-coupler $14_5$.

Each of the photo-couplers $14_1$ to $14_7$ once converts the inputted electric signal into a photo-signal, and then outputs the photo-signal as an electric signal. Namely, the video-signal processing device is optically coupled to the video processor 12 of the electronic endoscope, whereby the electronic endoscope is electrically isolated from various peripheral equipment connected to the electronic endoscope through the video-signal processing device according to the present invention.

The respective composite synchronizing signal (SYNC), red video signal (R), green video signal (G), and blue video signal (B) output from the photo-couplers $14_1$ to $14_4$ are amplified by the amplifiers $16_1$ to $16_4$, and the amplified signals (SYNC, R, G, B) are input to a digital-conversion processing circuit 18 including a timing generator circuit $20_1$; three analog-to-digital (A/D) converters $20_2$, $20_3$, and $20_4$; a color-conversion matrix circuit 22; a multiplexer 24; and a parallel-to-serial (P/S) converter 26.

In particular, the amplified composite synchronizing signal (SYNC) output from the amplifier $16_1$ is input to the timing generator circuit $20_1$, which produces a horizontal synchronizing signal, a vertical synchronizing signal, and several series of clock pulses having individual frequencies produced on the basis of the input composite synchronizing signal (SYNC).

Also, the respective amplified red video signal (R), green video signal (G), and blue video signal (B) output from the amplifiers $16_2$, $16_3$, and $16_4$ are input to the color-conversion matrix circuit 22, which produces a luminance signal (Y), and two kinds of color-difference signals $C_r$, $C_b$ ($C_r$=R-Y and $C_b$=B-Y) on the basis of the input color video signals (R, G, and B). Then, the luminance signal (Y), and the two kinds of color-difference signals ($C_r$ and $C_b$) are input to the A/D converters $20_2$, $20_3$, and $20_4$, in which the signals (Y, $C_r$, and $C_b$) are converted into 10-bit digital signals, respectively.

In this embodiment, the sampling of the 10-bit digital luminance signal (Y) from the A/D converter $20_2$ is carried out in accordance with a series of clock pulses of 13.5 MHz output from the timing generator circuit $20_1$. Also, the sampling of each 10-bit digital color-difference signal ($C_r$, $C_b$) from the A/D converters $20_3$ and $20_4$ are carried out in accordance with a series of clock pulses of 6.75 MHz output from the timing generator circuit $20_1$. Namely, the sampling frequency of the digital luminance signal is twice that of each digital color-difference signal ($C_r$, $C_b$)

The 10-bit digital signals (Y, $C_r$, and $C_b$) output from the A/D converters $20_2$, $20_3$, and $20_4$ are input to the multiplexer 24, which output the 10-bit digital signals (Y, $C_r$, and $C_b$) in regular sequence. In this embodiment, for example, the output of the 10-bit digital signals (Y, $C_r$, and $C_b$) may be sequentially carried out in the order of the luminance signal (Y), the color-difference signal ($C_r$), the luminance signal (Y), and the color-difference signal ($C_b$). Also, the sequential output of the 10-bit digital signals (Y, $C_r$, and $C_b$) is based upon a series of clock pulses of 27 MHz output from the timing generator circuit $20_1$. Note, the frequency of MHz is twice the sampling frequency of 13.5 MHz of the luminance signal (Y).

In this embodiment, over an effective image-period of a horizontal scanning line, the sampling of the digital luminance signals (Y) is carried out 720 times, and each of the samplings of the respective color-difference signals ($C_r$ and $C_b$) is carried out 360 times. Namely, a total sampling of 1,440 (720+2×360) samples of the digital signals (Y, $C_r$, and $C_b$) is obtained from the effective image-period of the horizontal scanning line.

Figure 3:
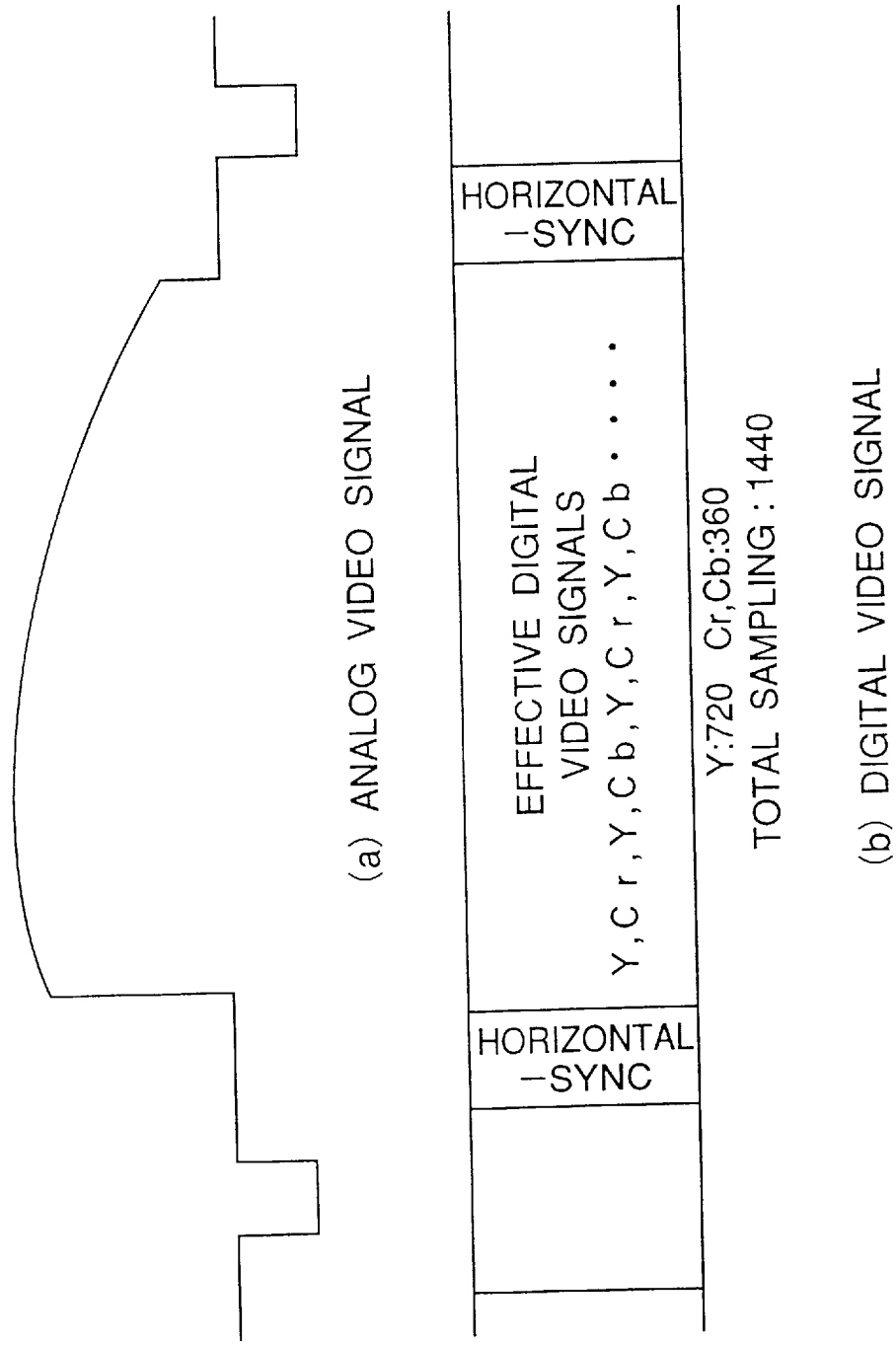
FIG. 3 is a conceptual view showing a relationship between an analog video signal of a horizontal scanning line and sampled digital signals obtained therefrom.

With reference to FIG. 3, a relationship between an analog video signal of a horizontal scanning line and sampled digital signals (Y, $C_r$, and C)$_b$ obtained therefrom is conceptually shown.

If the 10-bit digital signal (Y, $C_r$, $C_b$) are directly fed from the multiplexer 24 to a peripheral, the video-signal processing device and the peripheral must be connected to each other through a (parallel) signal cable having at least eleven signal lines. In this case, ten signal lines of the signal cable are used for the feeding of the 10-bit digital signal (Y, $C_r$, $C_b$), and the remaining single line is necessary for feeding a series of clock pulses. Of course, use of the signal cable having at least eleven signal lines is not preferable, especially, when the peripheral is not placed in site, i.e., when the peripheral is remote from the place at which the electronic endoscope is used, because a parallel signal cable having a plurality of signal lines is expensive.

According to the present invention, the parallel 10-bit digital signal (Y, $C_r$, $C_b$) output from the multiplexer 24 is input to the parallel-to-serial (P/S) converter 26, which converts the parallel 10-bit digital signal (Y, $C_r$, $C_b$) into a serial 10-bit digital signal in accordance with a series of driving clock pulses having a given frequency and output from the timing generator circuit $20_1$.

Figure 4:
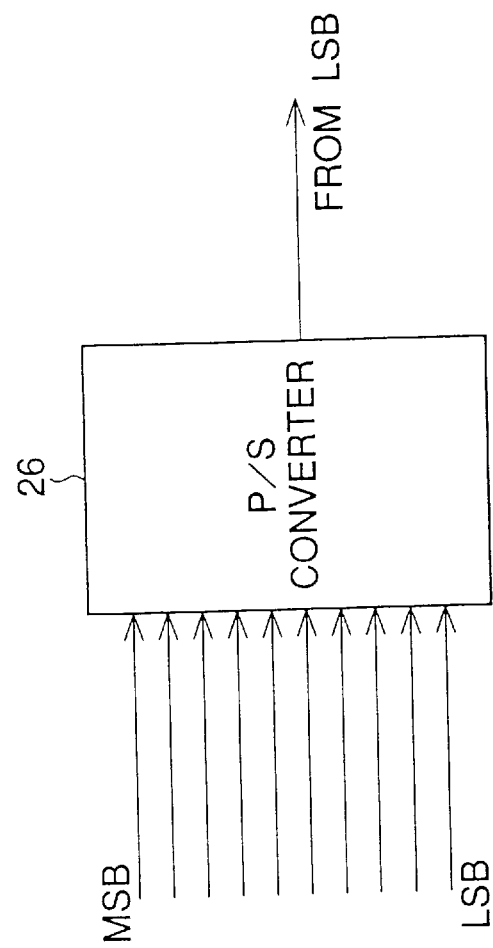
FIG. 4 is a block diagram showing a parallel-to-serial converter used in a digital-conversion processing circuit of the block diagram of FIG. 2.

As shown in FIG. 4, the conversion of the parallel 10-bit digital signal to the serial 10-bit digital signal is carried out in order from the least significant bit (LSB) to the most significant bit (MSB) . Namely, the serial 10-bit digital signal is output from the P/S converter 26 in such a manner that the least significant bit (LSB) and the most significant bit (MSB) are defined as a leading bit and a trailing bit, respectively.

Figure 5:
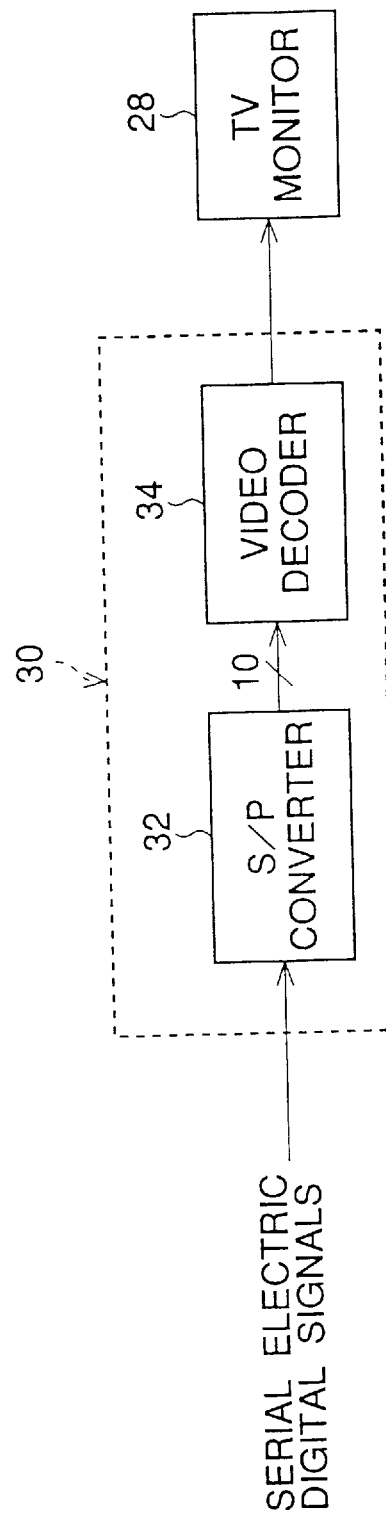
FIG. 5 is a block diagram of an analog-conversion processing device of a TV monitor to be connected to the video-signal processing device of FIG. 2.

FIG. 5 shows a TV monitor 28 as a peripheral, for example, installed at a monitor center of a hospital. The TV monitor 28 is intended to be connected to the P/S converter 26 of the digital-conversion processing circuit 18 of the video-signal processing device according to the present invention. The TV monitor 28 is provided with an analog-conversion processing circuit 30, in which the respective serial digital signals (Y, $C_r$, and $C_b$) fed from the P/S converter 26 thereto are converted into an analog red video signal (R), an analog green video signal (G), and an analog blue video signal (B).

Figure 6:
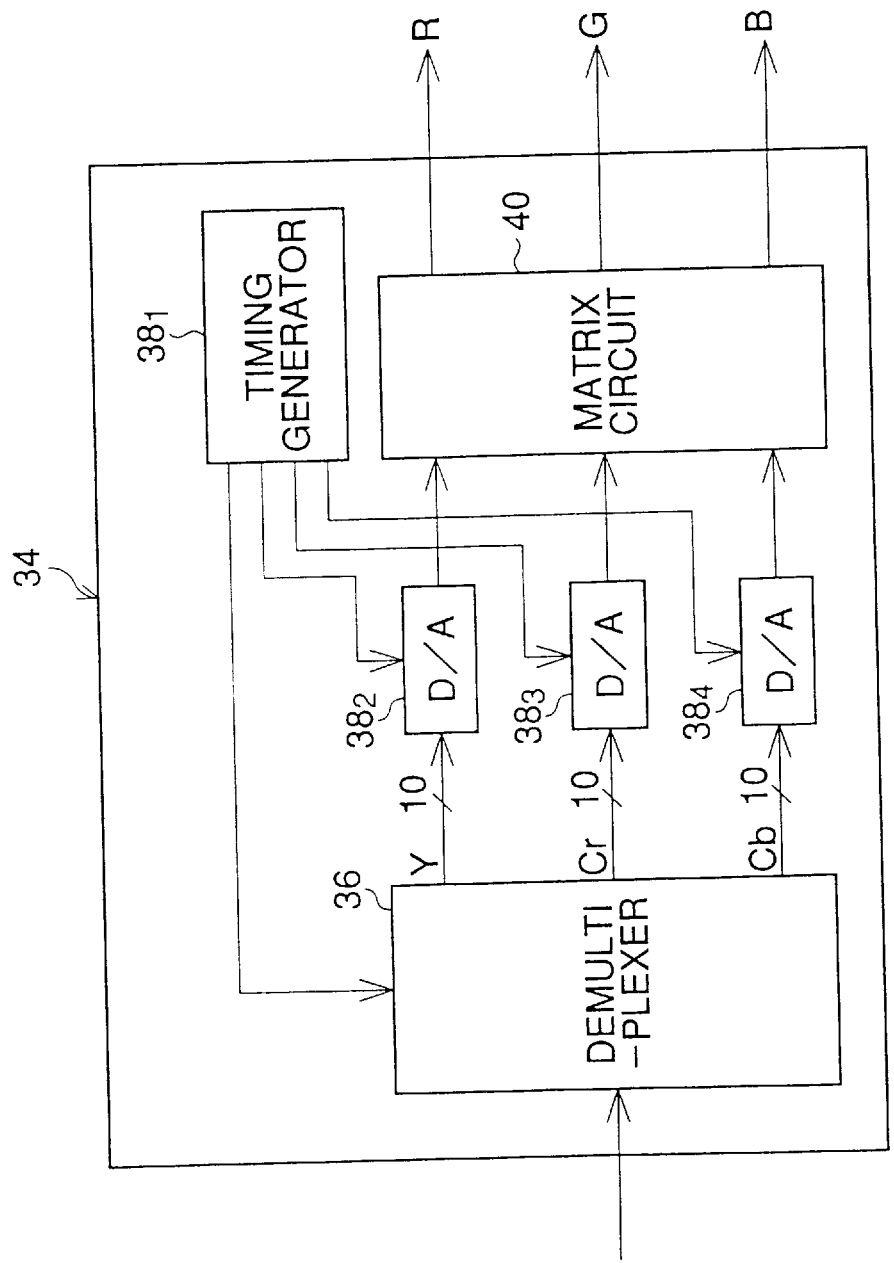
FIG. 6 is a block diagram of a video encoder included in the analog-conversion processing circuit shown in FIG. 5.

As shown in FIG. 5, the analog-conversion processing circuit 30 comprises a serial-to-parallel (S/P) converter 32, and a video decoder 34, and, as shown in FIG. 6, the video decoder 34 includes: a demultiplexer 36; a timing generator circuit $38_1$; a digital-to-analog (D/A) converters $38_2$, $38_3$, and $38_4$; and a color-conversion matrix circuit 40.

As it is apparent from the foregoing, the serial 10-bit digital signals (Y, $C_r$, and $C_b$) are sequentially fed from the P/S converter 26 to the analog-conversion processing circuit 30 in the order of the serial 10-bit digital luminance signal (Y), the serial 10-bit color-difference signal ($C_r$), the serial 10-bit digital luminance signal (Y), and the serial 10-bit digital color-difference signal ($C_b$). The serial 10-bit digital signal (Y, $C_r$, $C_b$) fed to the analog-conversion processing circuit 30 is input to the S/P converter 32, which converts the serial 10-bit digital signal (Y, $C_r$, $C_b$) into the parallel 10-bit digital signal (Y, $C_r$, $C_b$)

The parallel 10-bit digital signals (Y, $C_r$, and $C_b$) output from the S/P converter 32 are input to the demultiplexer 36, which distributes the 10-bit digital signals (Y, $C_r$, and $C_b$) to the D/A converters $38_2$, $38_3$, and $38_4$ in such a manner that the respective 10-bit luminance signal (&), 10-bit color-difference signal ($C_r$), and a 10-bit color-difference signal ($C_b$) are input to the D/A converters $38_2$, $38_3$, and $38_4$. The distribution of the 10-bit digital signals (Y, $C_r$, and $C_b$) to the D/A converts $38_2$, $38_3$, and $38_4$ is carried out in accordance with a series of clock pulses having a given frequency, which is output from the timing generator circuit $28_1$.

The respective D/A converters $38_2$, $38_3$, and $38_4$ convert the 10-bit digital signals (Y, $C_r$, $C_b$) into an analog luminance signal (Y), an analog color-difference signal ($C_r$), and an analog color-difference signal ($C_b$). The conversion of each 10-bit digital signal (Y, $C_r$, $C_b$) into the analog signal is carried out in accordance with a series of clock pulses having a given frequency, which is output from the timing generator circuit $38_1$ to the D/A converter $38_2$, $38_3$, $38_4$.

The analog signals (Y, $C_r$, and $C_b$) output from the respective D/A converters $38_2$, $38_3$, and $38_4$ are input to the color-conversion matrix circuit 40, in which the analog signals (Y, $C_r$, and $C_b$) are converted into an analog red video signal (R), an analog green video signal (G), and an analog blue video signal (B). These analog color video signals (R, G, and B) are fed from the color-conversion matrix circuit 40 to the TV monitor 28 to thereby reproduce a color image thereon.

Figure 7:
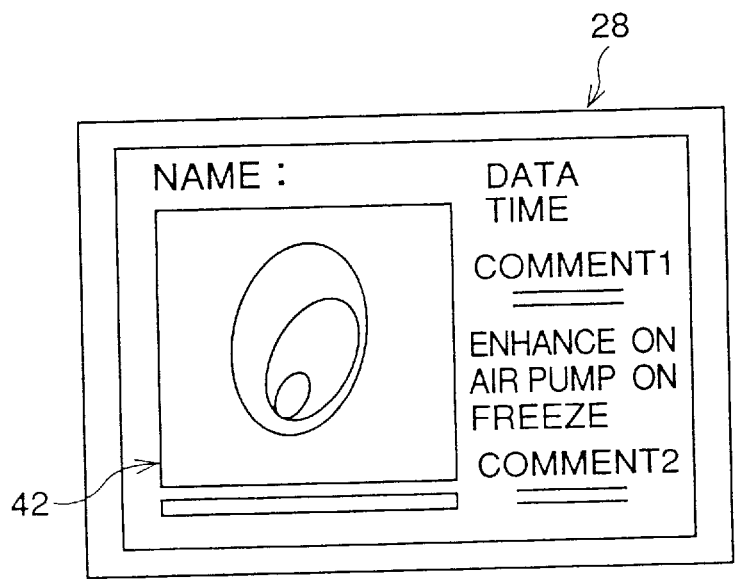
FIG. 7 is a front view of the TV monitor shown as a block in FIG. 5.

FIG. 7 shows images displayed on a screen of the TV monitor 28 by way of example. As shown in this drawing, an image photographed by the electronic endoscope is reproduced on a partial area or image-reproduction area 42 of the screen of the TV monitor 28, because the CCD image sensor used in the electronic endoscope is smaller than a CCD image sensor used in a usual TV camera. The full available area is not used for displaying the reproduced image; that is, the remaining area (except for the image-reproduction area 42) of the screen of the TV monitor 28 is not used for displaying the image, and a black area having no image information is available surrounding the reproduced image.

However, according to the present invention, the remaining black area of the screen of the TV monitor 28 is utilized as an area for displaying character-information data such as a patient's name, date/time, use-conditions of the electronic endoscope, messages or comments concerning the reproduced image and so on, as shown in FIG. 7.

Figure 8:
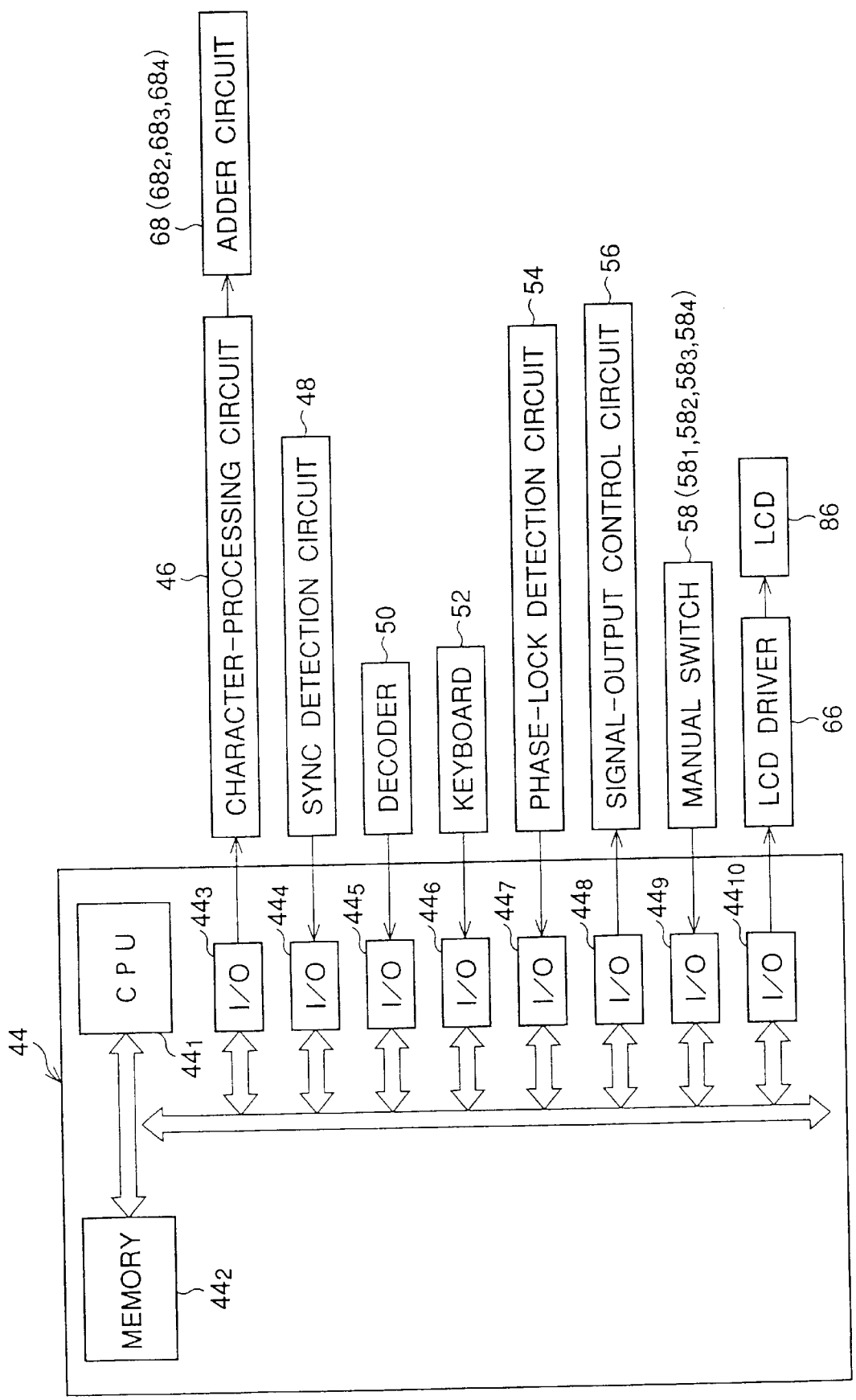
FIG. 8 is a block diagram of a control circuit included in the video-signal processing device shown in FIG. 2.

To this end, the video-signal processing device according to the present invention is provided with a control circuit 44, which may be formed as a microcomputer. That is, as shown in FIG. 8, the control circuit 44 comprises: a central processing unit (CPU) $44_1$; a memory $44_2$ connected to the CPU $44_1$ through a bus; and input/output (I/O) interface ports $44_3$ to $44_{10}$ connected to the CPU $44_1$ and the memory $44_2$ through the bus. Note, the memory $44_2$ includes a read-only memory (ROM) for storing programs, constants, etc., and a random access memory (RAM) for storing temporary data.

As it is apparent from FIG. 8, the respective I/O interface ports $44_3$ to $44_{10}$ are connected to a character-processing circuit 46, a synchronizing-signal detection circuit 48, a decoder 50, a keyboard 52, a phase-lock detection circuit 54, a signal-output control circuit 56, a switch 58, and a liquid crystal display (LCD) driver circuit 66.

The character-processing circuit 46 has an input terminal connected to the I/O interface port $44_3$, and an output terminal connected to an adder circuit 68, as shown in FIG. 8. Although the adder circuit 68 is merely shown as a block in FIG. 8, it represents three adder circuits $68_2$, $68_3$, and $68_4$ which are provided between the color-conversion matrix circuit 22 and the A/D converters $20_2$, $20_3$, and $20_4$, as shown in FIG. 2.

As shown in FIG. 2, the synchronizing-signal detection circuit 48 has an input terminal connected to the output side of the amplifier $16_1$, and two output terminals connected to the I/O interface port $44_4$ and the signal-output control circuit 56, respectively.

As shown in FIG. 2, the decoder 50 has an input terminal connected to an interface circuit 70, and two output terminals connected to the I/O interface port $44_5$ and the signal-output control circuit 56, respectively. It should be noted that the video processor 12 of the electronic endoscope is usually designed to be connected to a video-image processor computer, and the interface circuit 70 is placed in a position intervening therebetween.

Figure 9:
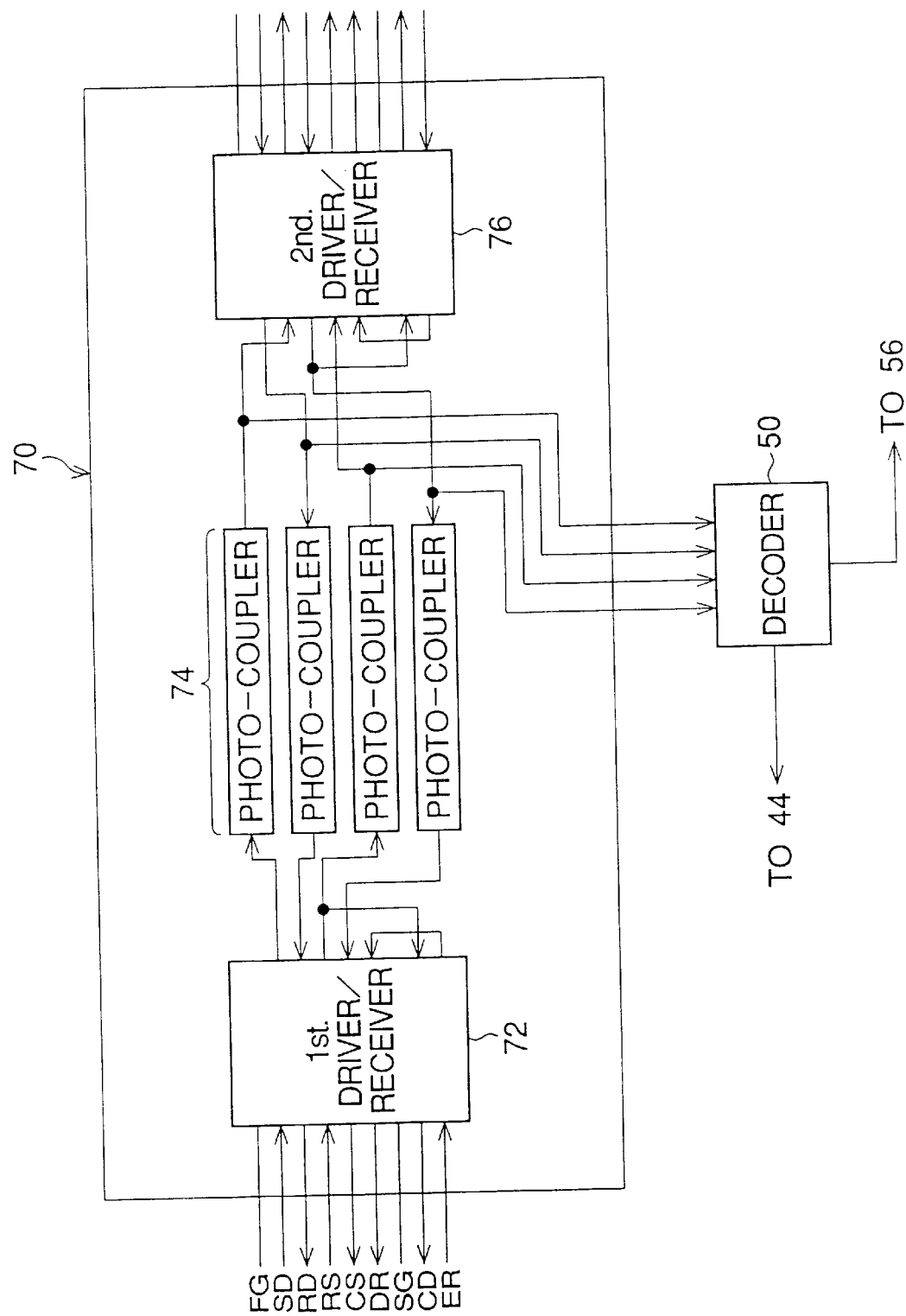
FIG. 9 is a block diagram of an interface circuit provided in the video-signal processing device shown in FIG. 2.

As shown in FIG. 9, the interface circuit 70, which may be arranged as an RS-232C interface, includes a first driver/receiver circuit 72, four photo-couplers 74, and a second driver/receiver circuit 76. The first driver/receiver circuit 72 is connected to signal lines (bus) extending from the video processor 12 of the electronic endoscope and indicated by references (FG, SD, RD, RS, CS, RD, SG, CD, and ER). Also, the first driver/receiver circuit 72 is connected to the second driver/receiver circuit 76 through the four photo-couplers 74, and the second driver/receiver circuit 76 is connected to the video-image processing computer through signal lines (bus) corresponding to the signal lines (FG, SD, RD, RS, CS, RD, SG, CD, and ER). Accordingly, the electronic endoscope is further electrically isolated from the video-image processing computer by the photo-couplers 74.

The keyboard 52 is operated by an operator (for example, a nurse) and various command signals and character-code data are input to the control circuit 44 through the I/O interface port $44_6$. The keyboard 52 is omitted from FIG. 2 to avoid a complex illustration.

The phase-lock detection circuit 54 has an input terminal connected to a phase-locked loop (PLL) 78, and two output terminals which are connected to the I/O interface port $44_7$ and the signal-output control circuit 56, respectively. The PLL 78 included in the timing generator circuit $20_1$ is used for the reasons stated hereinafter.

The signal-output control circuit 56 has four input terminals and three output terminals. As is apparent from the foregoing, three input terminals of the signal-output control circuit 56 are connected to the synchronizing-signal detection circuit 48, the decoder 50, and the phase-lock detection circuit 54, respectively, and the remaining input terminal is connected to the I/O interface port $44_8$. Also, one of the output terminals of the signal-output control circuit 56 is connected to the P/S converter 26, and the remaining two output terminals are connected a switch circuit 80 and a switch circuit 82, respectively, as shown in FIG. 2.

The switch circuit 80 is provided in the signal lines for the component-type color video signal composed of the composite synchronizing signal, red video signal, green video signal, and blue video signal, and the switch circuit 82 is provided in the signal lines for the component-type color video signal including the composite synchronizing signal, red video signal, green video signal, and blue video signal; the S-video signal composed of the luminance signal and amlitude-modulated (AM) color-difference signal; and the composite color video combined with the luminance signal and amlitude-modulated color-difference signal.

Although the switch 58 is merely shown as a block in FIG. 8, the shown block represents four ON/OFF switches $58_1$, $58_2$, $58_3$, and $58_4$ provided on a front panel 84 of the video-signal processing device, as shown in FIG. 2. Each of the switches $58_1$ to $58_4$ is manually operated by a user (for example, a doctor). As illustrated, a first terminal end of each switches $58_1$ to $58_4$ is connected to the I/O interface port $44_9$, and a second terminal end thereof is grounded. A voltage (VCC) is applied to the first terminal end of each switch $58_1$ to $58_4$. When each of the switches $58_1$ to $58_4$ is manually closed or turned ON, the potential (VCC) of the first terminal end is dropped to ground level.

The LCD driver circuit 66 is provided for driving a liquid crystal display (LCD) panel 86, on which various messages are displayed, as mentioned hereinafter.

To display the various character-information data on the remaining black area (except for the image-reproduction area 42) of the screen of the TV monitor 28, as shown in FIG. 7, suitable character-code data is outputted from the control circuit 44 to the character-processing circuit 46, which produces analog character-information signals on the basis of the character-code data inputted thereto. The respective analog character-information signals are output from the character-processing circuit 46 to the adder circuits $68_2$, $68_3$, and $68_4$, in which the respective analog character-information signals are added to the luminance video signal (Y) and color-difference video signals ($C_r$ and $C_b$) outputted from the color-conversion matrix circuit 22. A timing of the output of the analog character-information signals from the character-processing circuit 46 to the adder circuits $68_2$, 683, and 684 is defined on the basis of the detection of the composite synchronizing signal (SYNC) by the synchronizing-signal detection circuit 48.

In this embodiment, it is possible to display two kinds of character-information data on the remaining black area of the TV monitor 28: the first kind of character-information data is fixed character-information data produced on the basis of character-code data previously stored in the ROM of the control circuit 44; and the second kind of character-information data is variable (optional) character-information data produced on the basis of character-code data obtained via manipulation of the keyboard 52.

In particular, the electronic endoscope is provided with various function switches, such as an edge-enhancing switch, an air pump switch, a freeze-frame switch, and so on. When one of the function switches is turned ON, a fixed character-information data is displayed on the remaining black area of the screen of the TV monitor 28 as a message announcing that a function corresponding to the function switch concerned currently active.

For example, when the edge-enhancing switch is turned ON as one of the function switches, the video signals produced in the video processor 12 of the electronic endoscope is subjected to (known) edge-enhancing processing. At this time, the turned-ON signal of the edge-enhancing switch is fed as a digital control signal from the video processor 12 of the electronic endoscope to the interface circuit 70, and is input to the first driver/receiver circuit 72 thereof.

Then, the turned-ON signal is outputted from the first driver/receiver circuit 72 to the decoder 50 through the photo-couplers 74, and is converted into predetermined data in the decoder 50. The converted data is output from the encoder 50 to the control circuit 44, in which character-code data corresponding to the converted data is read from the ROM thereof. The read character-code data is output from the control circuit 44 to the character-processing circuit 46.

The character-processing circuit 46 produces analog character-information signals on the basis of the character-code data input thereto. Then, the respective analog character-information signals are output from the character-processing circuit 46 to the adder circuits $68_2$, $68_3$, and $68_4$, in which the respective analog character-information signals are added to the luminance video signal (Y) and color-difference video signals ($C_r$ and $C_b$) outputted from the color-conversion matrix circuit 22.

Thus, as shown in FIG. 7, a message "ENHANCE ON" is displayed on the remaining black area of the screen of the TV monitor 28 as fixed character-information data for announcing that the reproduced image displayed on the image-reproduction area 42 is subjected to edge-enhancing processing.

Also, when the flexible conduit 10 of the electronic endoscope is inserted into the stomach of a patient for a medical inspection, and when the air pump switch is turned ON as one of the function switches, an air pump (not shown) included in the video processor 12 is actuated to feed air to inflate the stomach. At this time, similarly to the edge-enhancing switch, the turned-ON signal of the air pump switch is fed as a digital control signal from the video processor 12 of the electronic endoscope to the interface circuit 70, displaying a message "AIR PUMP ON" on the remaining black area of the screen of the TV monitor 28 as fixed character-information data for announcing that the reproduced stomach image displayed on the image-reproduction area 42 is that of a stomach inflated due to the turning-ON of the air pump switch.

Furthermore, when the freeze-frame switch is turned ON as one of the function switches, the reproduced image is frozen as a still picture. At this time, similarly to the edge-enhancing switch, the turned-ON signal of the freezing switch is fed as a digital control switch from the video processor 12 of the electronic endoscope to the interface circuit 70, displaying a message "FREEZE" on the remaining black area of the screen of the TV monitor 28 as fixed character-information data for announcing that the reproduced image displayed on the image-reproduction area 42 is a (freeze-frame) still picture.

Figure 10:
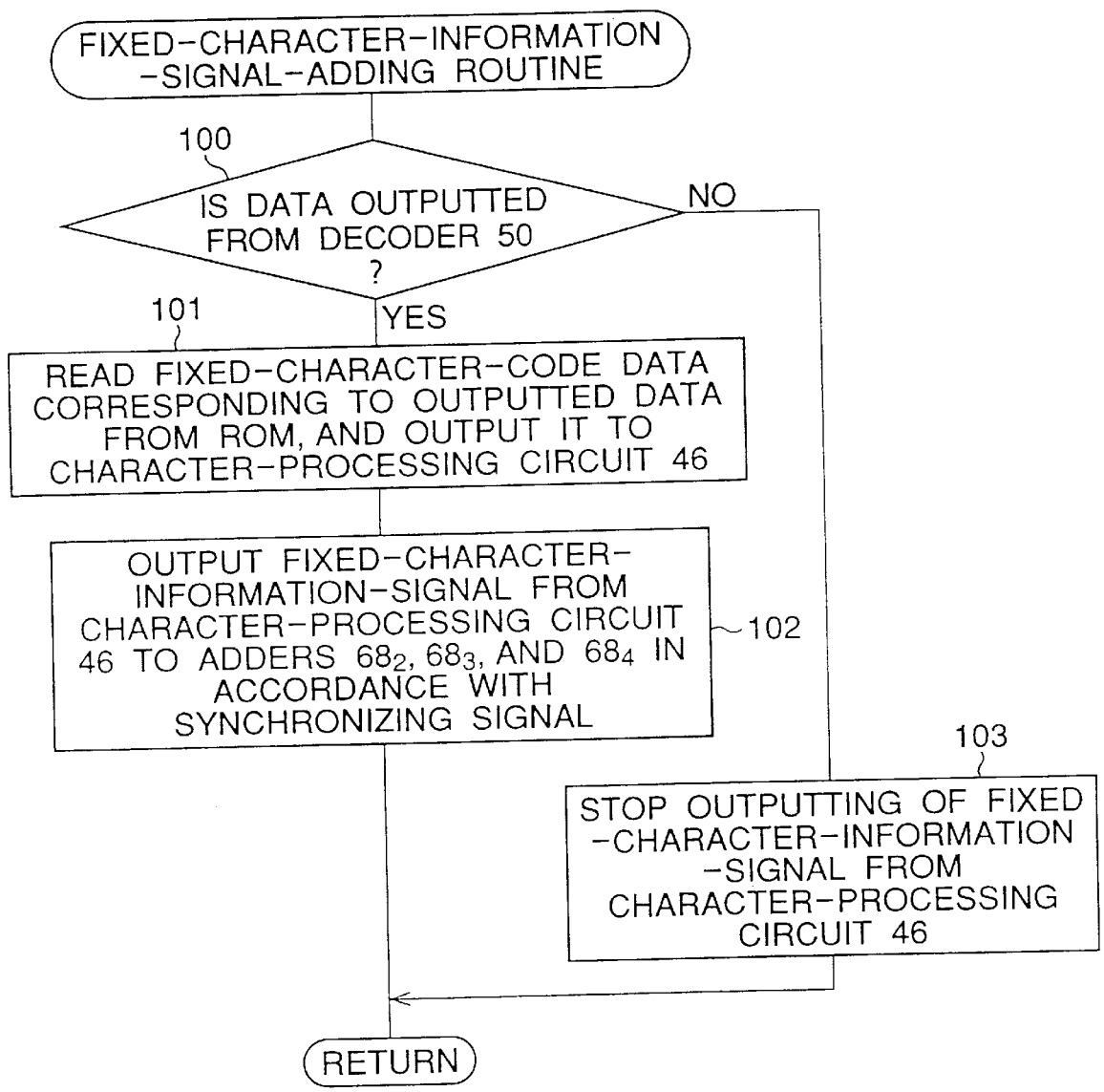
FIG. 10 is a flowchart showing a routing for adding a fixed character-information signal to a luminance signal and two kinds of color difference video signals.

FIG. 10 is a flowchart showing a routine for adding a fixed character-information signal to the luminance signal (Y) and color difference video signals ($C_r$ and $C_b$). This routine is, for example, a time-based interrupt routine executed at regular intervals in the control circuit 44.

At step 100, it is determined whether or not given data is outputted from the decoder 50 to the control circuit 44. As mentioned above, when one of the function switches of the electronic endoscope is turned ON, this turned-ON signal is input to the encoder 50 through the interface circuit 70.

When the output of the data from the decoder 50 is confirmed, the control proceeds to step 101, in which fixed character-code data corresponding to the data output from the decoder 50 is read from the ROM of the control circuit 44. For example, when the data output from the decoder 50 is derived from the turned-ON signal of the edge-enhancing switch, the fixed character-code data read from the ROM corresponds to the message "ENHANCE ON" to be displayed. Then, the fixed character-code data read from the ROM is output to the character-processing circuit 46, which produces a character-information signal.

At step 102, the produced character-information signal is output from the character-processing circuit 46 to the adder circuits $68_2$, $68_3$, and $68_4$, and is added to the luminance video signal (Y) and color difference video signals ($C_r$ and $C_b$).

At step 100, when the output of the data from the encoder 50 is stopped, i.e., when the function switch is turned OFF, the control proceeds from step 100 to step 103, in which the output of the character-information signal from the character-processing circuit 46 to the adder circuits $68_2$, $68_3$, and $68_4$ is stopped.

On the other hand, variable (optional) character-information data to be displayed on the remaining black area of the TV monitor is input by an operator manipulating the keyboard 52, for example, on the basis of a doctor's comments made during his medical inspection.

In particular, character-code data obtained through the manipulation of the keyboard 54 is output from the control circuit 44 to the character-processing circuit 46, in which analog character-information signals are produced on the basis of the character-code input thereto. Then, the respective analog character-information signals are output from the character-processing circuit 46 to the adder circuits $68_2$, $68_3$, and $68_4$, in which the respective analog character-information signals are added to the luminance video signal (Y) and color-difference video signals ($C_r$ and $C_b$) outputted from the color-conversion matrix circuit 22.

Thus, as shown in FIG. 7, messages (although represented by "COMMENT 1" and "COMMENT 2" any text may appear) are displayed on the remaining black area of the screen of the TV monitor 28 as variable (optional) character-information data.

Furthermore, as shown in FIG. 7, as a part of the variable (optional) character-information data, a patient's name, a date/time, and so on may be displayed on the remaining black area of the screen of the TV monitor 28.

Figure 11:
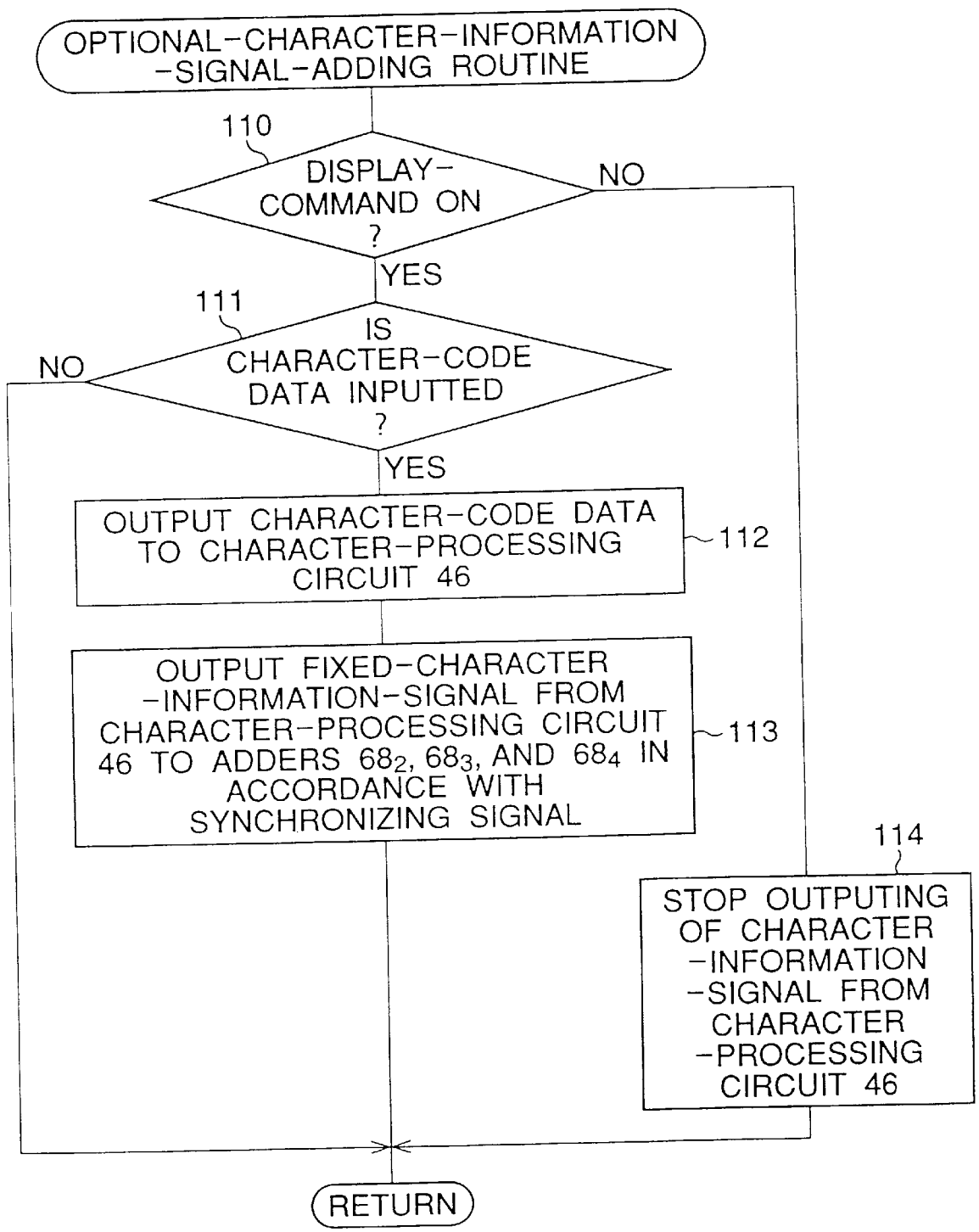
FIG. 11 is a flowchart showing a routing for adding a variable optional character-information signal to a luminance signal and two kinds of color difference video signals.

FIG. 11 is a flowchart showing a routine for adding variable (optional) character-information signal to the luminance signal (Y) and color difference video signals ($C_r$ and $C_b$). This routine also is a time-based interrupt routine executed at regular time intervals in the control circuit 44.

At step 110, it is determined whether or not a display-command signal is turned ON or changed from a low level to a high level. The change of the display-command signal from the low level to the high level is performed by manipulating the keyboard 52.

When the turned-ON status of the display-command signal is confirmed, control proceeds to step 111, in which it is determined whether or not variable (optional) character-code data is made by manipulating the keyboard 52.

When the keyboard input of the character-code data is confirmed, the control proceeds to step 112, in which the keyboard input character-code data is output from the control circuit 44 to the character-processing circuit 46, which produces a character-information signal.

At step 113, the produced character-information signal is output from the character-processing circuit 46 to the adder circuits $68_2$, $68_3$, and $68_4$, and is added to the luminance video signal (Y) and color difference video signals ($C_r$ and $C_b$).

At step 110, when the display-command signal is turned OFF or changed from the high level to the low level, the control proceeds from step 110 to 114, in which the output of the character-information signal from the character-processing circuit 46 to the adder circuits $68_2$, $68_3$, and $68_4$ is stopped.

As is apparent from the foregoing, according to the present invention, even though the TV monitor 28 may be located at a monitor center remote from where the electronic endoscope is used, doctors can make a proper medical inspection at the monitor center on the basis of the reproduced image and of the character-information data displayed on the screen of the TV monitor 28.

Before the reproduction of the color image can be properly carried out on the screen of the TV monitor 28, a phase of the outputting frequency of the serial 10-bit digital signal (Y, $C_r$, $C_b$), i.e., a phase of the driving clock pulses for the P/S converter 26 is made to coincide with a phase of the composite synchronizing signal (SYNC). To this end, the timing generator circuit $20_1$ is provided with the above-mentioned phase-locked loop (PLL) circuit 78.

Figure 12:
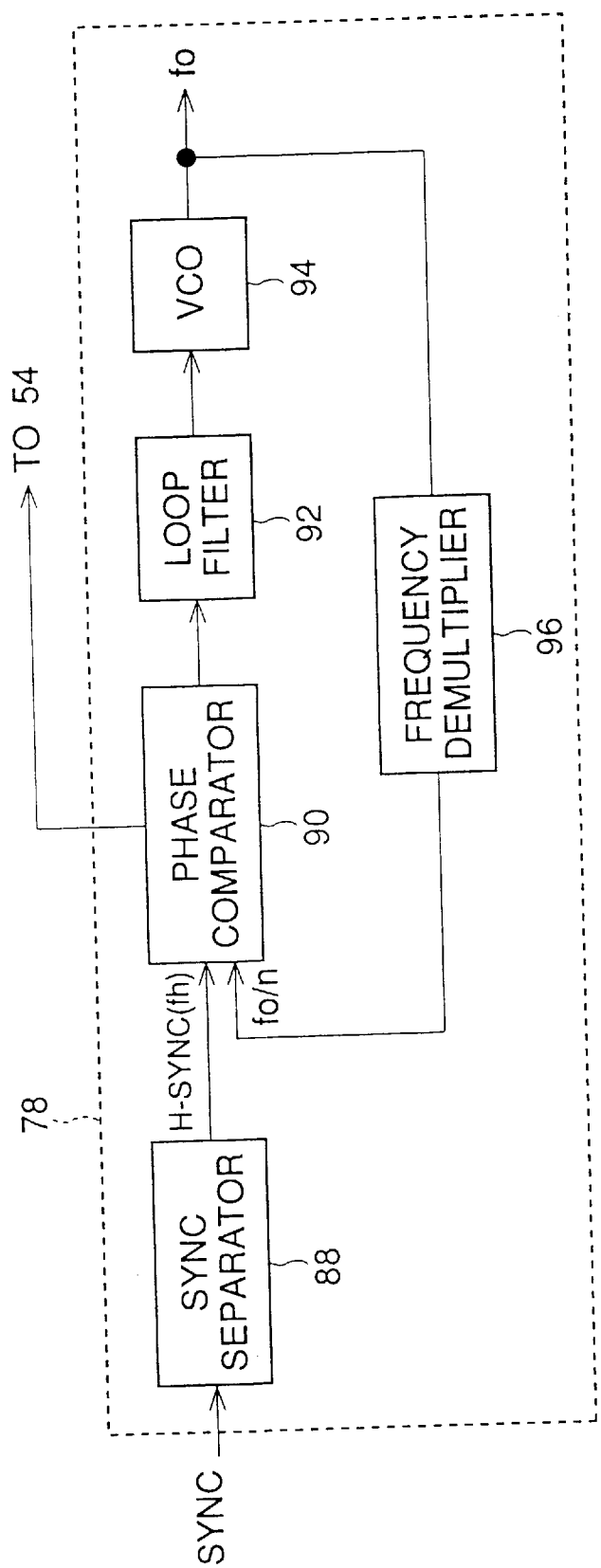
FIG. 12 is a block diagram of a phase-locked loop circuit included in a timing generator circuit shown in FIG. 2.

In particular, as shown in FIG. 12, the PLL circuit 78 includes a composite-synchronizing-signal separator 88; a phase comparator 90; a loop filter 92; a voltage controlled oscillator (VC) 94; and a frequency divider 96. The amplified composite synchronizing signal (SYNC) output from the amplifier $16_1$ is input to the composite-synchronizing separator 88, in which a horizontal synchronizing signal (H-SYNC) having a given frequency ($f_h$) is separated from the composite synchronizing signal (SYNC). Then, the separated horizontal synchronizing signal (H-SYNC) having the given frequency (fh) is input to the phase comparator 90.

On the other hand, the VC 94 outputs a series of clock pulses having a given frequency ($f_0$), which is divided by the frequency divider 96 into a series of clock pulses having a frequency ($f_0/n$). As used herein, "n" is a suitable integer (as described later). Then, series of divided clock pulses having a frequency ($f_0/n$) is input to the phase comparator 90.

At the phase comparator 90, the frequency ($f_h$) of the horizontal synchronizing signal (H-SYNC) is compared with the frequency ($f_0$) of the clock pulses, and a difference between the frequencies ($f_h$ and $f_0$) is output from the phase comparator 90 as a voltage signal representing a phase difference between the horizontal synchronizing signal (H-SYNC) and the divided clock pulses having the frequency ($f_0/n$). Then, the voltage signal is input to the loop filter 92, in which the voltage signal is filtered so as to eliminate high-frequency noises therefrom.

The filtered voltage signal is input to the VC 94, in which the frequency ($f_0$) of the clock pulses output therefrom is changed on the basis of the input voltage signal in such a manner that the difference between the frequency ($f_h$) of the horizontal synchronizing signal and the frequency ($f_0/n$) of the divided clock pulses is reduced. Thus, when a level of the voltage signal output from the phase comparator 90 becomes zero, the phase of the clock pulses output from the VC 94 is made to coincide with the phase of the horizontal synchronizing signal (H-SYNC), and the frequency ($f_0$) thereof is n (integer) times the frequency ($f_h$) of the horizontal synchronizing signal (H-SYNC).

In practice, if the NTSC color system is introduced in the electronic endoscope, the integer "n" is equal to 1,716, and if the PAL color system is introduced in the electronic endoscope, the integer "n" is equal to 1,782.

The series of clock pulses output from the VCO 94 and having the phase coincided with the phase of the horizontal synchronizing signal (H-SYNC) is input to the P/S converter 26 as the driving clock pulses for the operation of the P/S converter 26. In particular, the series of clock pulses input to the P/S converter 26 is further divided into a series of clock pulses having a frequency 10×n times the frequency ($f_h$) of the horizontal synchronizing signal (H-SYNC), and the conversion of the parallel 10-bit digital signal (Y, $C_r$, $C_b$) into the serial 10-bit signal is carried out on the basis of the series of clock pulses having the frequency 10×n times the frequency ($f_h$) of the horizontal synchronizing signal (HSYNC), due to the serial feeding of the 10-bit digital signal (Y, $C_r$, $C_b$). Thus, the proper reproduction of the color image on the TV monitor 28 can be ensured.

As is apparent from FIGS. 2 and 12, the phase comparator 90 is connected to a phase-lock detection circuit 54, which monitors whether or not the level of the voltage signal output from the phase comparator 90 becomes zero. Namely, the phase-lock detection circuit 54 detects a phase-lock, i.e., a coincidence of the phase of the divided clock pulses with the phase of the horizontal synchronizing signal (H-SYNC). For example, when the level of the voltage signal output from the phase comparator 90 becomes zero, i.e., when the phase-lock is obtained in the phase comparator 90, a phase-lock voltage signal output from the phase comparator 90 to the phase-lock detection circuit 54 is changed from a low level to a high level.

As shown in FIG. 2, the phase-lock detection circuit 54 is connected to a signal-output control circuit 56, and a detection voltage signal is output from the phase-lock detection circuit 54 to the signal-output control circuit 56. When the phase-lock detection circuit 54 detects the change of the phase-lock voltage signal from the low level to the high level, the phase-lock detection circuit 54 changes the detection voltage signal from a low level to a high level.

The signal-output control circuit 54 is connected to the P/S converter 26, and a disabling/enabling voltage signal is output from the signal-output control circuit 56 to the P/S converter 26. When the detection voltage signal output from the phase-lock detection circuit 54 to the signal-output control circuit 56 is changed from the low level to the high level, the disabling/enabling voltage signal is also changed from a low level to a high level.

In short, while the phase-lock detection circuit 54 does not detect the phase-lock, the disabling/enabling voltage signal is kept at the low level, and, while the phase-lock detection circuit 54 detects the phase-lock, the disabling/enabling voltage signal is kept at the low level.

While the disabling/enabling voltage signal is kept at the low level, the operation of the P/S converter 26 is disabled, whereby the P/S converter 26 outputs no serial digital signal. Namely, only while the disabling/enabling voltage signal is kept at the high level, the operation of the P/S converter 26 is enabled, whereby the P/S converter 26 can output the serial digital signal (Y, $C_r$, $C_b$). Accordingly, a turbulent image cannot be reproduced on the TV monitor 28, because the serial digital signals (Y, $C_r$, and $C_b$) cannot be fed to the TV monitor 28 until the phase of the driving clock pulses for the P/S converter 26 is made to coincide with the phase of the horizontal synchronizing signal (H-SYNC). Also, even when the video-signal processing device is connected to the electronic endoscope in such a manner that the connection between the signal lines for the composite synchronizing signal (SYNC) is established after the connections between the respective red, green, and blue video signal lines for the red video signal (R), green video signal (G), and blue video signal (B) are established, a turbulent image is not reproduced on the TV monitor 28.

Figure 13:
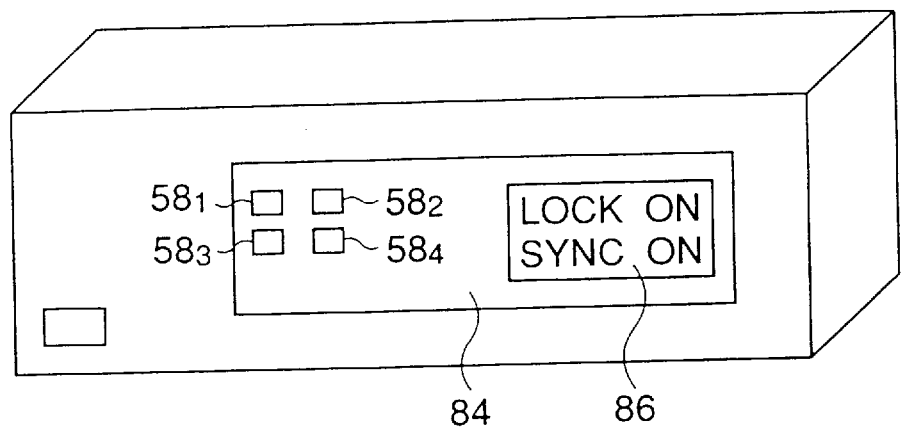
FIG. 13 is a schematic perspective view showing an external appearance of the video-signal processing device shown in FIG. 2.

Also, the phase-lock detection circuit 54 outputs the phase-lock detection voltage signal to the control circuit 44. When the phase-lock detection voltage signal is changed into the low level to the high level, i.e., when the phase-lock is detected by the phase-lock detection switch 54, the control circuit 44 operates the LCD driver circuit 66 on the basis of the change of the phase-lock detection voltage signal from the low level to the high level, so that a message "LOCK ON" is displayed on the LCD panel 86 for announcing the detection of the phase-lock, as shown in FIG. 13, which schematically illustrates an external view of an embodiment of the video-signal processing device according to the present invention.

Similarly, the synchronizing-signal detection circuit 48 outputs the synchronizing-signal detection voltage signal to the control circuit 44. When the synchronizing-signal detection voltage signal is changed from the low level to the high level, i.e., when the output of the composite synchronizing signal (SYNC) from the amplifier $20_1$ is detected by the synchronizing-signal detection switch 48, the control circuit 44 operates the LCD circuit 66 on the basis of the change of the synchronizing-signal detection voltage signal from the low level to the high level, so that a message "SYNC ON" is displayed on the LCD panel 86, for announcing the detection of the output of the composite synchronizing signal (SYNC), as shown in FIG. 13.

In this embodiment, it is possible to forcibly stop the feeding of the serial digital signals (Y, $C_r$, and $C_b$) from the P/S converter 26 to the TV monitor 28, if necessary. For example, when a doctor considers a reproduction of image on the outside TV monitor 28 undesirable, the feeding of the serial digital signals (Y, $C_r$, and $C_b$) from the P/S converter 26 to the TV monitor 28 is stopped by manipulating the switch $58_1$.

In particular, when the switch $58_1$ is closed or turned ON to thereby drop the potential (VCC) of the first terminal end to the grounded level, the disabling/enabling voltage signal output from the signal-output control circuit 56 to the P/S converter 26 is forcibly changed from the high level to the low level even if the phase of the driving clock pulses for the P/S converter 26 coincides with the phase of the horizontal synchronizing signal (H-SYNC). Thus, the feeding of the serial digital signals (Y, $C_r$, and $C_b$) from the P/S converter 26 to the TV monitor 28 can be forcibly stopped.

As shown in FIG. 2, the video-signal processing device is also arranged such that the component-type color video signal (SYNC, R, G, and B), the S-video signal, and the composite video signal are fed to suitable peripheral equipment. In this embodiment, the output of each analog color video signals may be forcibly stopped, if necessary. To this end, a first switch circuit 80 is provided in the signal lines for the red video signal (R), green video signal (G), and blue video signal (B), and a second switch circuit 82 is provided in all the signal lines for the component-type color video signal (SYNC, R, G, and B), the S-video signal, and the composite video signal.

The first switch circuit 80 is connected to the signal-output control circuit 56, which performs ON/OFF control of the switch circuit 80 on the basis of the detection voltage signal output from the synchronizing-signal detection circuit 48.

In particular, when the output of the composite synchronizing signal from the amplifier $16_1$ is detected by the synchronizing-signal detection circuit 48, the detection voltage signal output from the synchronizing-signal detection circuit 48 to the signal-output control circuit 56 is changed from a low level to a high level. At this time, an ON/OFF control voltage signal output from the signal-output control circuit 56 to the switch circuit 80 is also changed from a low level to a high level.

While the ON/OFF control voltage signal is kept at the low level, the switch circuit 80 is turned OFF, disabling the output of the analog red video signal, green video signal, and blue video signal from the video-signal processing device.

While the ON/OFF control voltage signal is kept at the high level, the switch circuit 80 is turned ON, whereby enabling the output of the analog red video signal, green video signal, and blue video signal from the video-signal processing device.

Accordingly, when the video-signal processing device is connected to the electronic endoscope in such a manner that the connection between the signal lines for the composite synchronizing signal (SYNC) is established after the connections between the respective red, green, and blue video signal lines for the red video signal (R), green video signal (G), and blue video signal (B) are established, the feeding of uncontrollable video signals from the video-signal processor device to peripheral equipment is securely prevented.

The switches $58_2$, $58_3$, and $58_4$ operate the second switch circuit 82 through the intermediary of the signal-output control circuit $56_7$ to selectively stop the outputting of three kinds of analog color video signals from the video-signal processing device. Similarly to the switch $58_1$, the switches $58_2$, $58_3$, and $58_4$ also are manipulated by an operator, for example, a doctor.

When the switch $58_2$ is closed or turned ON to thereby drop the potential (VCC) of the first terminal end to the grounded level, the signal-output control circuit 56 operates the switch circuit 82 such that the feeding of the composite synchronizing signal (SYNC), red video signal, green video signal, and blue video signal to peripheral equipment is forcibly stopped.

Also, when the switch $58_3$ is closed or turned ON to thereby drop the potential (VCC) of the first terminal end to the grounded level, the signal-output control circuit 56 operates the switch circuit 82 such that the feeding of the luminance signal and amplitude-modulated color-difference signal to peripheral equipment is forcibly stopped. Further, when the switch $58_4$ is closed or turned ON to thereby drop the potential (VCC) of the first terminal end to the grounded level, the signal-output control circuit 56 operates the switch circuit 82 such that the feeding of the composite color video signal to peripheral equipment is forcibly stopped.

Preferably, each of the manual switches $58_1$, $58_2$, $58_3$, and $58_4$ provided on the front panel 84 is formed as a push-button type switch, as shown in FIG. 13, and a push button element thereof is preferably performed of a semi-transparent material. The push button element incorporates or is associated with a suitable light source such as a light-emitting diode (LED). When any one of the manual switches $58_1$, $58_2$, $58_3$, and $58_4$ is turned ON, the corresponding LED is electrically energized. Thus, it is possible to easily know the video signal of which the output is stopped. Namely, each of the LED's associated with the manual switches $58_1$, $58_2$, $58_3$, and $58_4$ serves as an indicator indicating whether or not the corresponding manual switch is turned ON.

The video-imaging processing computer connected to the electronic endoscope through the interface circuit 70 may be placed at a place where the electronic endoscope is used, or may be installed at another place such as a monitor center of a hospital, remotely located from the place where the electronic endoscope is used. In the latter case, it is preferable to forcibly stop the feeding of the serial digital video signals (Y, $C_r$, and $C_b$) from the video-signal processing device at the monitor center side. For example, there may be a case where a connection of a TV monitor of the monitor center is changed from the video-signal processing device concerned to a video-signal processing device connected to an electronic endoscope used in another place.

To this end, the decoder 50 is connected to the signal-output control circuit 56. When a command signal for stopping the feeding of the serial digital video signals (Y, $C_r$, and $C_b$) from the P/S converter 26 is fed from the video-image processing computer to the video-signal processing device, the command signal is input to the decoder 50 through the interface circuit 70. Upon inputting the command signal to the decoder 50, a voltage signal output from the decoder 50 to the signal-output control circuit 56 is changed from a low level to a high level, forcibly changing the disabling/enabling signal from the high level to the low level. Thus, the feeding of the serial digital video signals (Y, $C_r$, and $C_b$) from the P/S converter 26 to the TV monitor is forcibly stopped.

The video-signal processing device as mentioned above is placed in a position intervening between the electronic endoscope and various peripheral equipment such as a TV monitor, a video tape recorder, a printer, a video-image processing computer and so on. The electronic endoscope is electrically isolated from the peripheral equipments by the photo-couplers ($14_1$ to $14_7$; 74) of the video-signal processing device according to the present invention.

According to the present invention, the serial digital video signals (Y, $C_r$, and $C_b$) output from the digital-conversion processing circuit 18 can be fed to the TV monitor 28 through a coaxial cable having a single signal line, which is cheaper than the parallel signal cable having at least eleven single lines as mentioned above. Also, even though the TV monitor 28 may be remote from the place where the electronic endoscope is used, a clear and proper reproduction of color images on the TV monitor 28 can be ensured, because the video signal is fed to the TV monitor 28 as a digital video signal.

Figure 14:
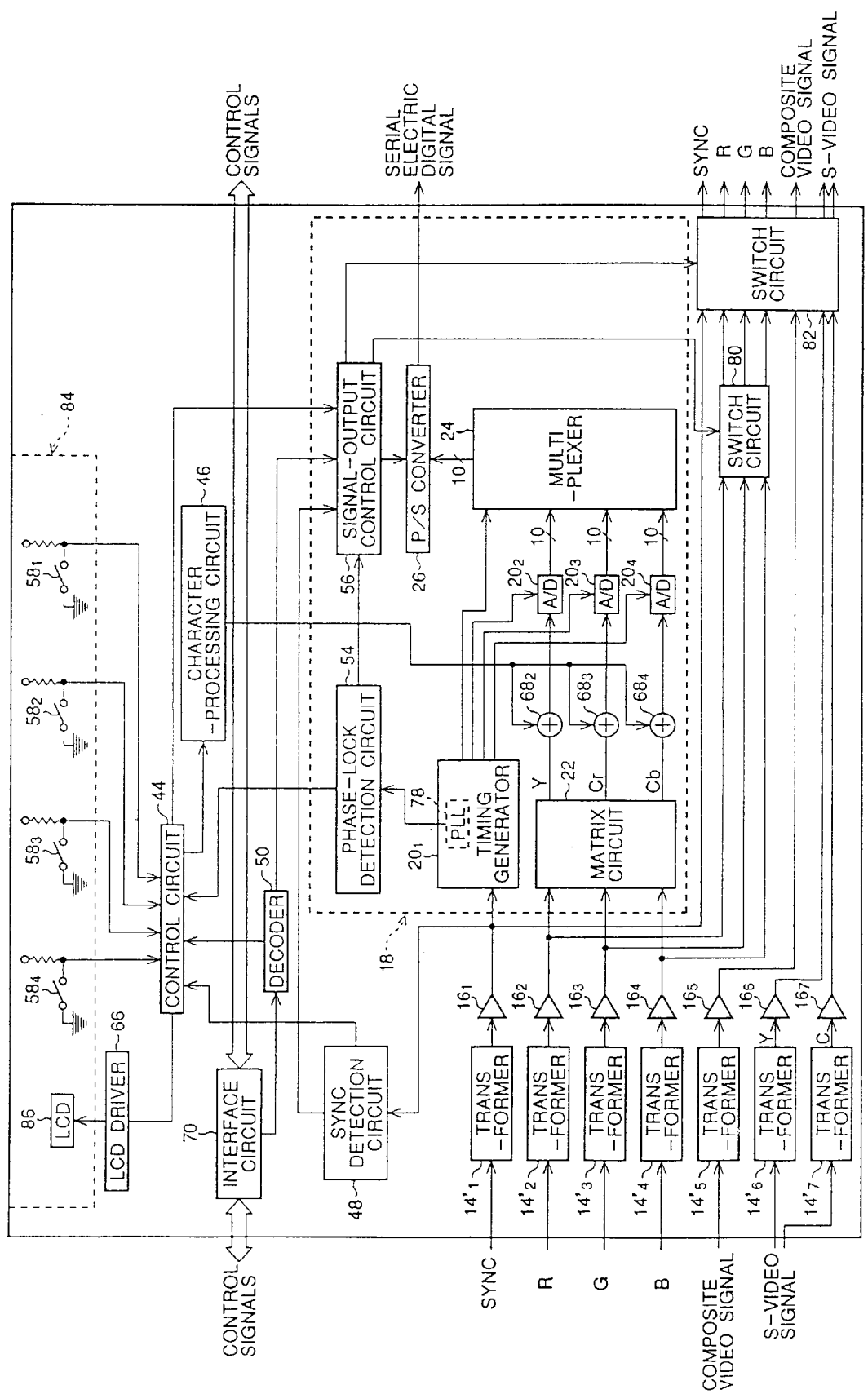
FIG. 14 is a block diagram showing a second embodiment of the video-signal processing device according to the present invention.

FIG. 14 shows a second embodiment of the video-signal processing device according to the present invention. In this drawing, features similar to those of FIG. 2 are indicated by the same reference numerals. The second embodiment is similar to the first embodiment of FIG. 2, except that seven transformers $14_1'$ to $14_7'$ are substituted for the photo-couplers $14_1$ to $14_7$.

In the second embodiment, the respective primary windings of the transformers $14_1'$ to $14_7'$ are connected to the output lines of the video processor 12 of the electronic endoscope, and the respective secondary windings of transformers $14_1'$ to $14_7'$ are connected to the amplifiers $16_1$ to $16_7$. Thus, the electronic endoscope is electrically isolated from the video-signal processing device. Note, the photo-couplers 74 of the interface circuit 79 (FIG. 9) may be replaced by transformers in a similar manner.

Figure 15:
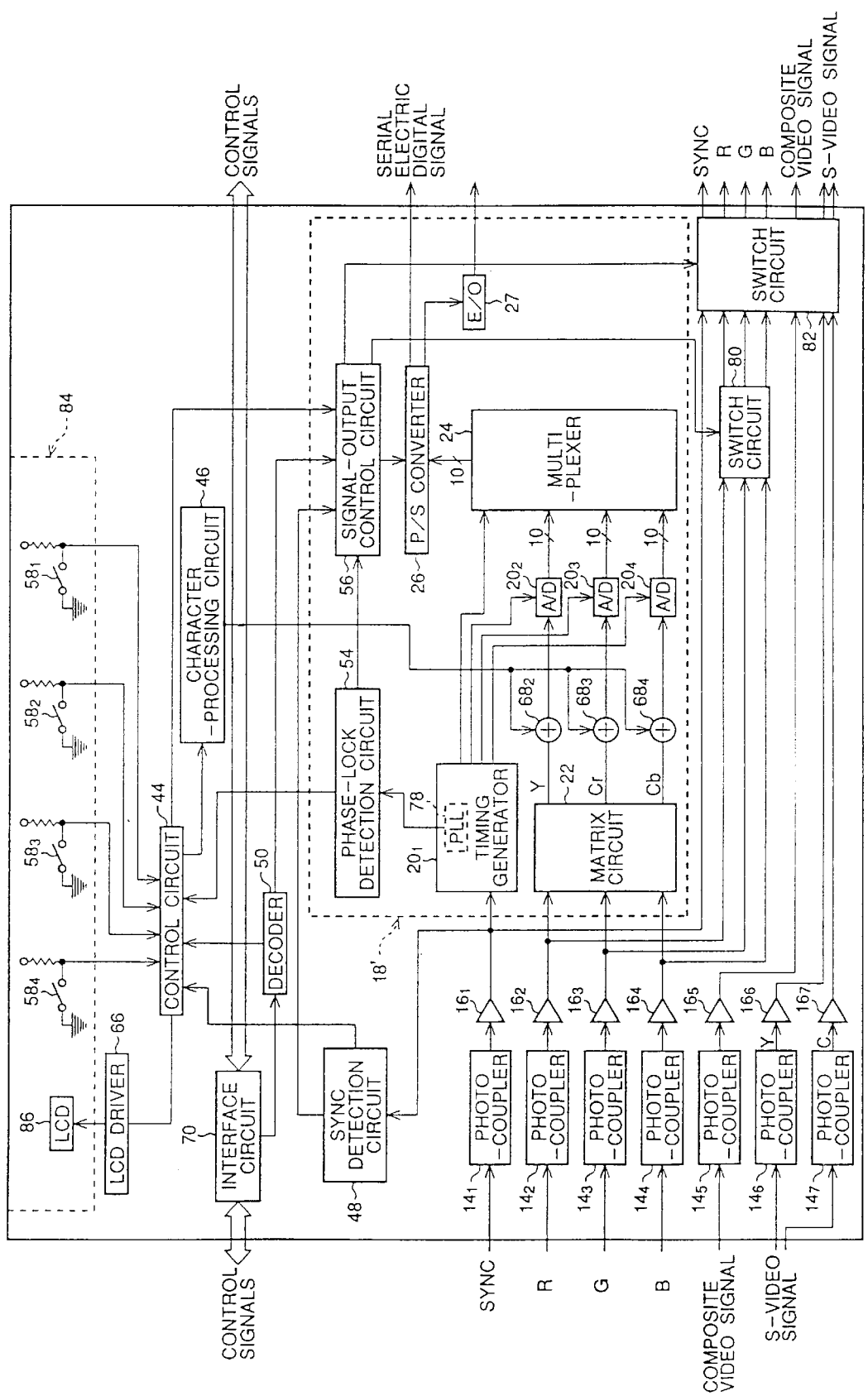
FIG. 15 is a block diagram showing a third embodiment of the video-signal processing device according to the present invention.

FIG. 15 shows a block diagram of a third embodiment of the video-signal processing device according to the present invention. In this drawing, features similar to those of FIG. 2 are indicated by the same reference numerals. The third embodiment is similar to the first embodiment of FIG. 2 except that a digital-conversion processing circuit 18' of the former further includes an electrical-optical (E/O) converter 27 connected to the P/S converter 26, to thereby convert the respective serial electric digital signals (Y, $C_r$, and $C_b$) into serial optical digital signals (Y, $C_r$, and $C_b$). That is, in the third embodiment, the digital-conversion processing circuit 18 can output not only serial electric digital signals (Y, $C_r$, and $C_b$) but also serial optical digital signals (Y, $C_r$, and $C_b$).

Figure 16:
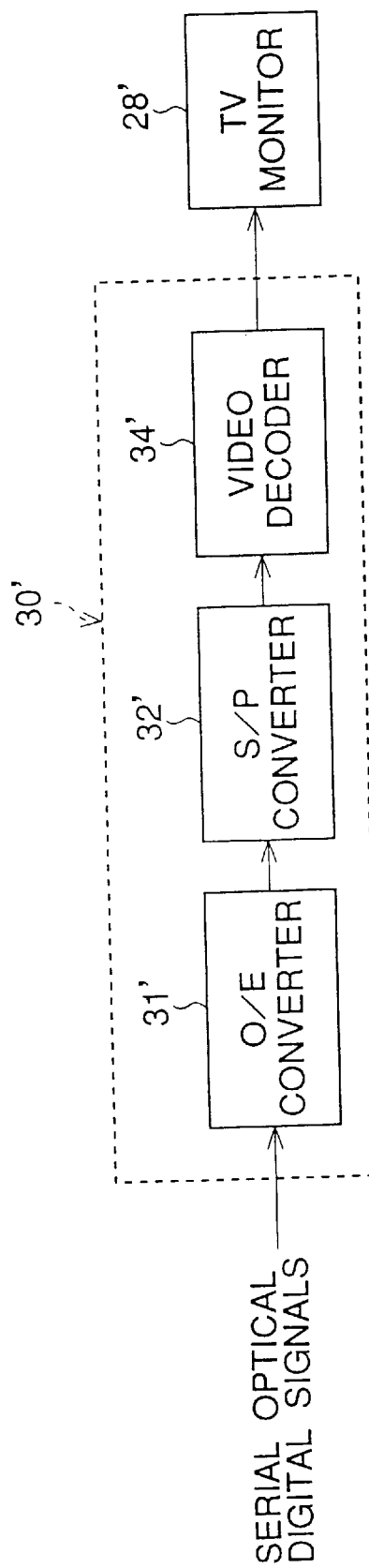
FIG. 16 is a block diagram of an analog-conversion processing circuit of a TV monitor to be connected to the video-signal processing device shown in FIG. 15.

FIG. 16 shows a TV monitor 28' as peripheral equipment, which is intended to be connected to the E/O converter 27 of the digital-conversion processing circuit 18' through an optical fiber cable. To this end, the TV monitor 28' is provided with an analog-conversion processing circuit 30', in which the respective serial optical digital signals (Y, $C_r$, and $C_b$) fed from the E/O converter 27 through the optical fiber cable are converted into an electric analog red video signal (R), an electric analog green video signal (G), and an electric analog blue video signal (B).

As shown in FIG. 16, the analog-conversion processing circuit 30' comprises an optical-electrical (O/E) converter 31', a serial-to-parallel (S/P) converter 32', and a video decoder 34'. Note, the video decoder 34' is identical with the video decoder 34 shown in FIG. 5.

The serial optical digital signals (Y, $C_r$, and $C_b$) are sequentially fed from the E/O converter 27 to the analog-conversion processing circuit 30' in the order of the serial optical digital luminance signal (Y), the serial optical color-difference signal ($C_r$), the serial optical digital luminance signal (Y), and the serial optical digital color-difference signal ($C_b$). The serial optical digital signal (Y, $C_r$, $C_b$) fed to the analog-conversion processing circuit 30' is inputted to the O/E converter 31', which converts the serial optical digital signal (Y, $C_r$, $C_b$) into the serial electric digital signal (Y, $C_r$, $C_b$).

The serial electric digital signals (Y, $C_r$, and $C_b$) outputted from the O/E converter 31' are input to the S/P converter 32', which converts the serial electric digital signals (Y, $C_r$, and $C_b$) into parallel electric digital signals (Y, $C_r$, and $C_b$). These parallel digital signals (Y, $C_r$, and $C_b$) outputted from the S/P converter 32' are input to the video decoder 34', in which the parallel digital signals (Y, $C_r$, $C_b$) are processed in substantially the same manner as in the video decoder 34 (FIG. 5), whereby the video decoder 34' outputs an analog red video signal (R), an analog green video signal (G), and an analog blue video signal (B) to the TV monitor 28' to thereby reproduce a color image thereon.

The optical fiber cable used to feed the serial optical digital signals (Y, $C_r$, and $C_b$) from the E/O converter 27 to the analog-conversion processing circuit 30' has a signal-feed loss lower than that of the coaxial cable used to feed the serial electric digital signals (Y, $C_r$, and $C_b$) from the P/S converter to the analog-conversion processing circuit 30 (FIG. 5). Accordingly, the third embodiment is preferred when a peripheral such as the TV monitor 28' is remote from the place where the electronic endoscope is used. Also, peripheral equipment such as the TV monitor 28' can be more securely isolated from the electronic endoscope by the optical fiber cable therebetween.

Figure 17:
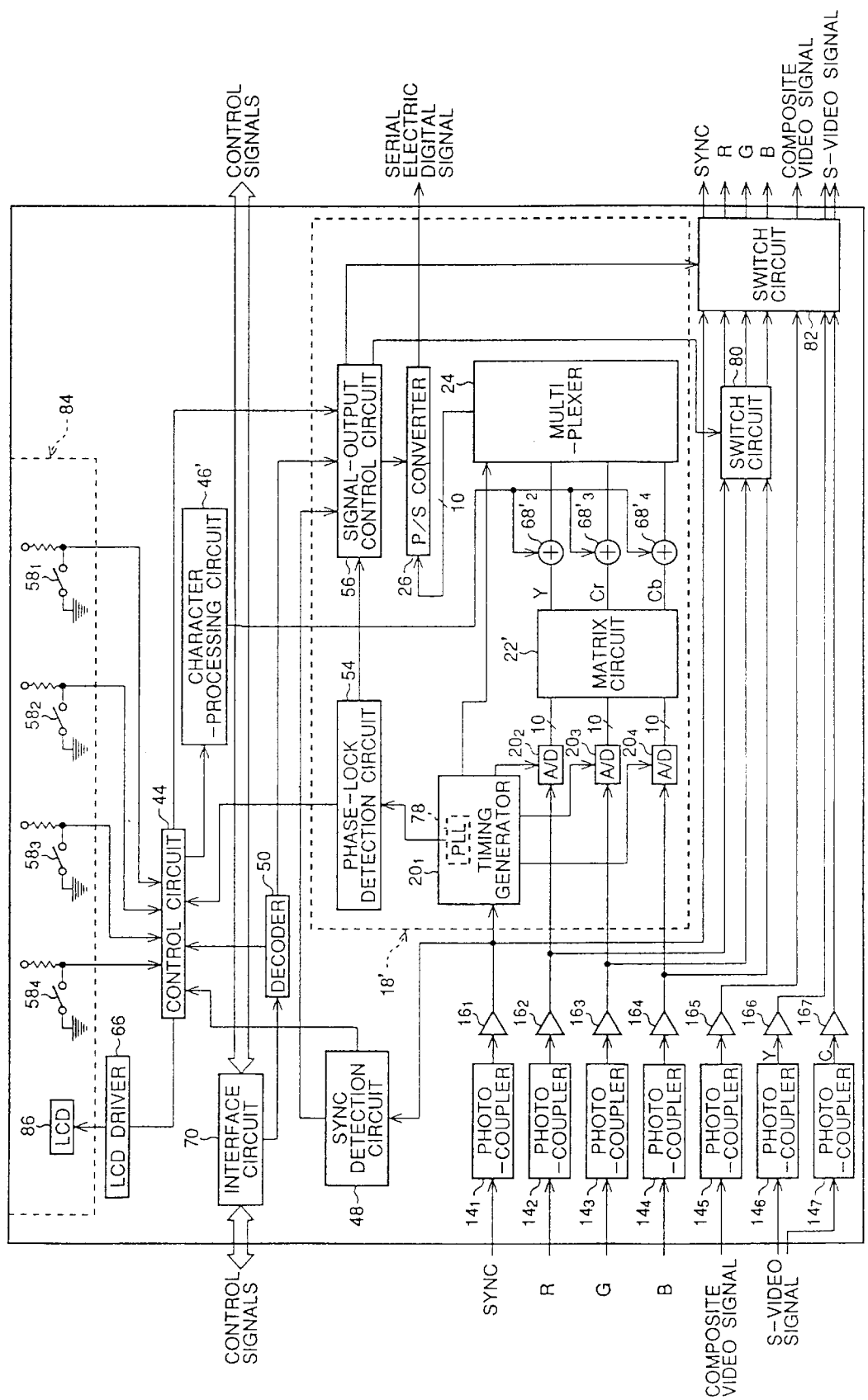
FIG. 17 is a block diagram showing a fourth embodiment of the video-signal processing device according to the present invention.

FIG. 17 shows a fourth embodiment of the video-signal processing device according to the present invention. In this drawing, features similar to those of FIG. 2 are indicated by the same reference numerals. The fourth embodiment is similar to the first embodiment of FIG. 2 except that, in a digital-conversion processing circuit 18', a digital color-conversion matrix circuit 22'; four digital adders $68_2'$ to $68_4'$; and a digital character-processing circuit 46' are substituted for the color-conversion analog matrix circuit 22; the analog adders $68_2$ to $68_4$; and the analog character-processing circuit 46, respectively. As shown in FIG. 17, the digital color-conversion matrix circuit 22' and the digital adders $68_2'$ to $68_4'$ are disposed between the A/D converters $20_2$ to $20_4$ and the multiplexer 24.

In the fourth embodiment, the respective red video signal (R), green video signal (G), and blue video signal (B) output from the amplifiers $16_2$ to $16_4$ are input to the A/D converters $20_2$ to $20_4$, which converts the video signals (R, G, and B) into 10-bit digital signals (R, G, and B). Then, the respective 10-bit digital color video signal (R, G, and B) output from the A/D converters $20_2$ to $20_4$ are input to the digital color-conversion matrix circuit 22', which produces a digital luminance signal (Y), and two kinds of digital color-difference signals $C_r$, $C_b$ ($C_r$=R–Y and $C_b$=B–Y) on the basis of the input color digital video signals (R, G, and B). Thus, the digital luminance signal (Y), and two kinds of digital color-difference signals ($C_r$ and $C_b$) output from the digital color-conversion matrix circuit 22' input to the adder circuits $68_2'$, $68_3'$, and $68_4'$.

On the other hand, the digital character-processing circuit 46' produces digital character-information signals on the basis of the character-code data output from the control circuit 44 thereto. Then, the respective digital character-information signals are output from the character-processing circuit 46 to the digital adder circuits $68_2'$, $68_3'$, and $68_4'$, in which the respective digital character-information signals are added to the digital luminance video signal (Y) and digital color-difference video signals ($C_r$ and $C_b$) output from the digital color-conversion matrix circuit 22'.

Accordingly, the 10-bit digital luminance signal (Y), and the two kinds of 10-bit color-difference signals ($C_r$ and $C_b$) are processed in substantially the same manner as in the first embodiment of FIG. 2.

Figure 18:
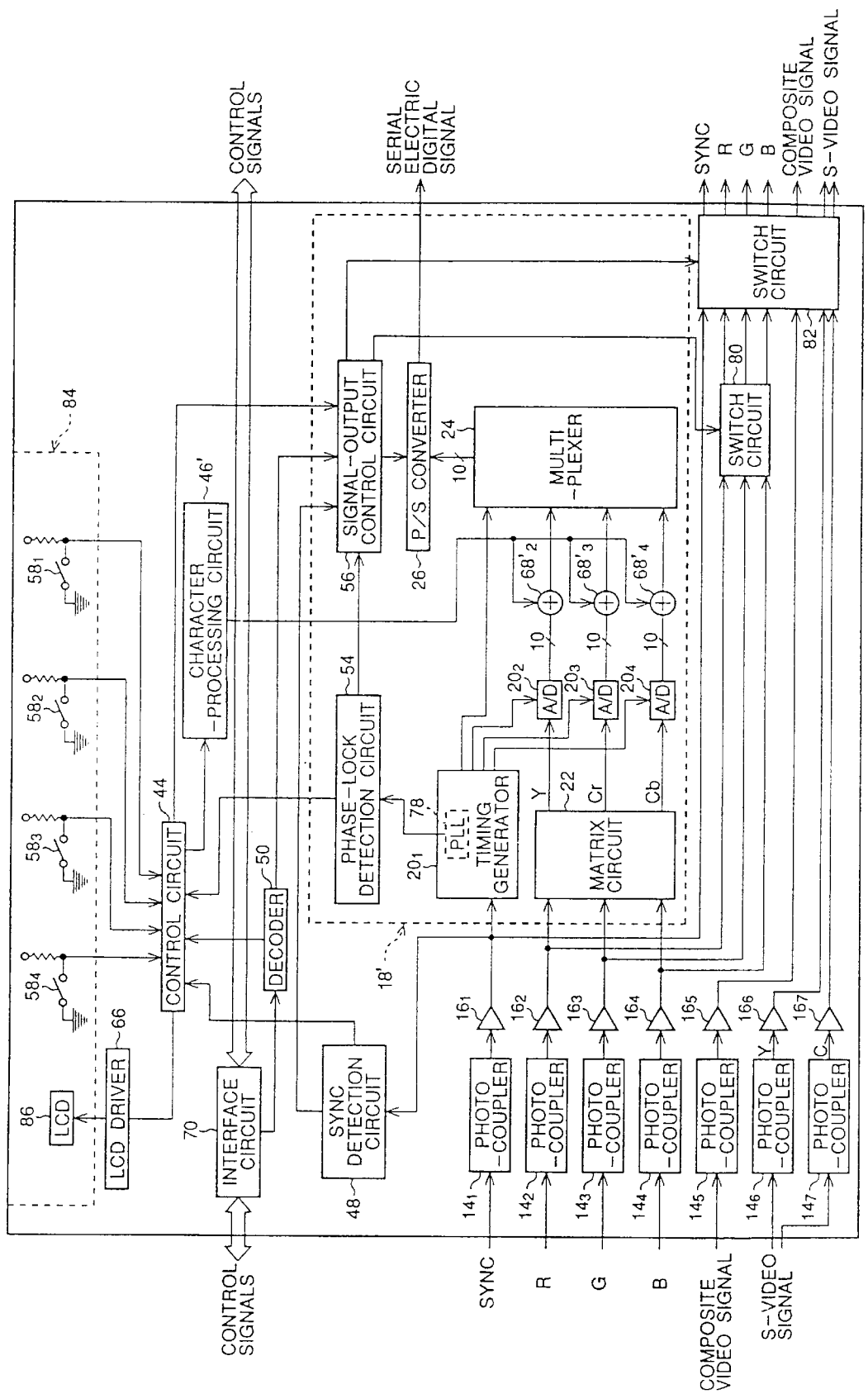
FIG. 18 is a block diagram showing a fifth embodiment of the video-signal processing device according to the present invention.

FIG. 18 shows a fifth embodiment of the video-signal processing device according to the present invention. In this drawing, features similar to those of FIG. 2 are indicated by the same reference numerals. The fifth embodiment is similar to the first embodiment of FIG. 2 except that, in a digital-conversion processing circuit 18', four digital adders $68_2'$ to $68_4'$; and a digital character-processing circuit 46' are substituted for the analog adders $68_2$ to $68_4$; and the analog character-processing circuit 46, respectively. As shown in FIG. 18, the digital adders $68_2'$ to $68_4'$ are disposed between the A/D converters $20_2$ to $20_4$ and the multiplexer 24.

In the fifth embodiment, the respective red video signal (R), green video signal (G), and blue video signal (B) outputted from the amplifiers $16_2$ to $16_4$ are input to the analog color-conversion digital matrix circuit 22, which produces an analog luminance signal (Y), and two kinds of analog color-difference signals $C_r$, $C_b$ ($C_r$=R–Y and $C_b$=B–Y) on the basis of the input analog color video signals (R, G, and B). Then, the analog luminance signal (Y), and two kinds of analog color-difference signals ($C_r$ and $C_b$) are input to the A/D converters $20_2$ to $20_4$, which converts the analog luminance signal (Y), and two kinds of analog color-difference signals ($C_r$ and $C_b$) into 10-bit digital video signals (Y, $C_r$, and $C_b$). Thus, the respective 10-bit color digital video signals (R, G, and B) output from the A/D converters $20_2$ to $20_4$ are input to the digital adder circuits $68_2'$, $68_3'$, and $68_4'$.

On the other hand, the digital character-processing circuit 46' produces digital character-information signals on the basis of the character-code data output from the control circuit 44 thereto. Then, the respective digital character-information signals are output from the character-processing circuit 46 to the digital adder circuits $68_2'$, $68_3'$, and $68_4'$ in which the respective digital character-information signals are added to the digital luminance video signal (Y) and digital color-difference video signals ($C_r$ and $C_b$) output from the digital color-conversion matrix circuit 22'.

Accordingly, the 10-bit digital luminance signal (Y), and the two kinds of 10-bit color-difference signals ($C_r$ and $C_b$) are processed in substantially the same manner as in the first embodiment of FIG. 2.

Figure 19:
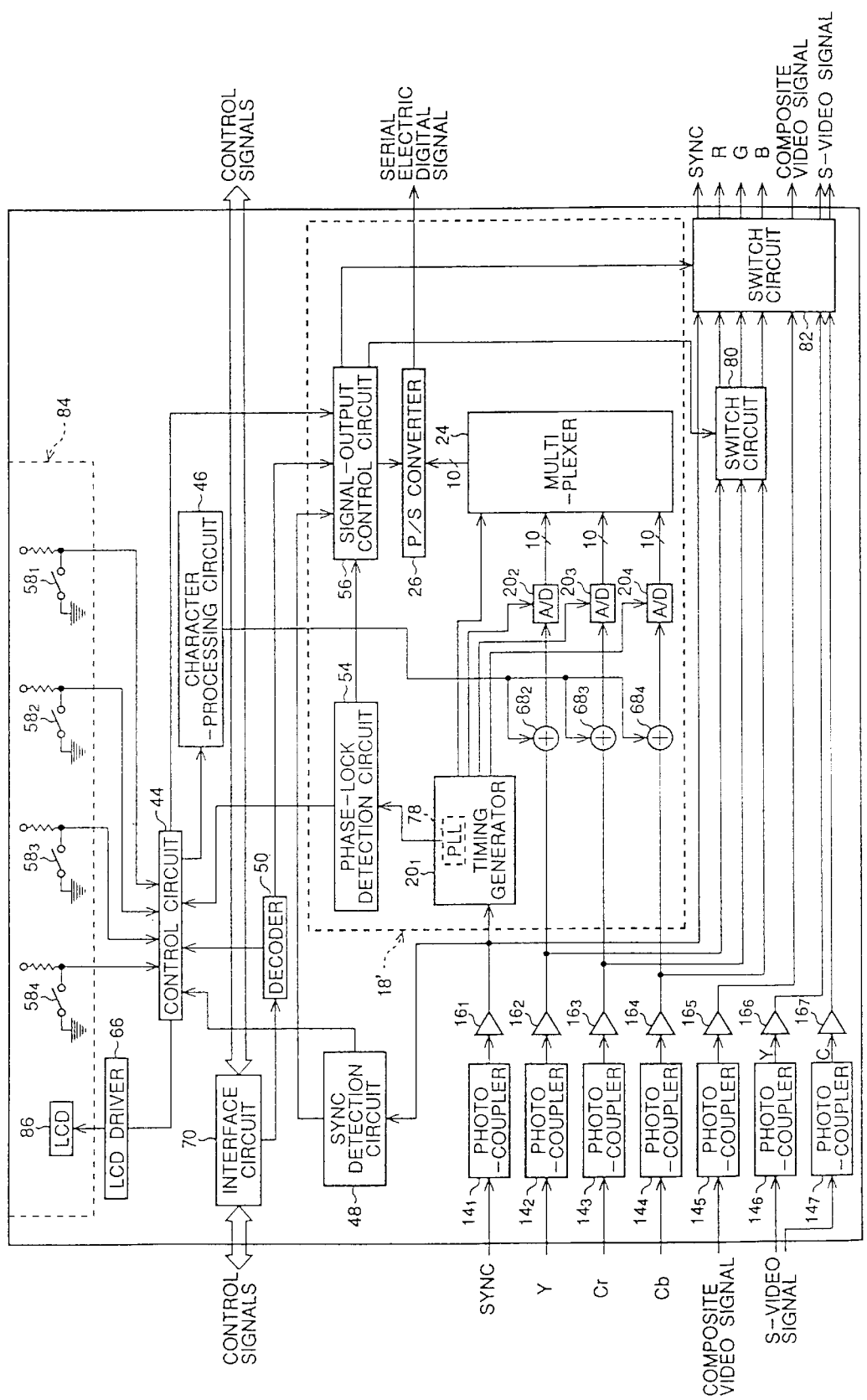
FIG. 19 is a block diagram showing a sixth embodiment of the video-signal processing device according to the present invention.

FIG. 19 shows a sixth embodiment of the video-signal processing device according to the present invention. In this drawing, features similar to those of FIG. 2 are indicated by the same reference numerals. The sixth embodiment is similar to the first embodiment of FIG. 2 except that the color-conversion analog matrix circuit 22 is eliminated from a digital-conversion processing circuit 18'.

The sixth embodiment is connectable to an electronic endoscope which is arranged so as to output another component-type color video signal, including a luminance signal (Y), and two kinds of color-difference signals ($C_r$ and $C_b$), from the video processor thereof. Thus, in the sixth embodiment, the color-conversion analog matrix circuit (22) is unnecessary.

Finally, it will be understood by those skilled in the art that the foregoing description is of preferred embodiments of the device and that various changes and modifications may be made to the present invention without departing from the spirit and scope thereof.

The present disclosure relates to subject matter contained in Japanese Patent Application No. 8-149917 (filed on May 21, 1996), which is expressly incorporated herein, by reference, in its entirety.

We claim:

1. A video-signal processing apparatus connectable to an electronic endoscope designed to output at least one kind of video signal, the electronic endoscope further outputting a control signal in response to a turning-ON of a function switch, said apparatus comprising:

a memory for storing fixed character-code data;

a memory-reading device that reads the fixed character-code data from said memory in response to the control signal output from the electronic endoscope;

a character-information signal producing device that produces a fixed character-information signal on the basis of the fixed character-code data read from said memory;

an adder for adding the character-information signal to the video signal output from the electronic endoscope; and an output device from which the video signal carrying the character-information signal is fed from said apparatus.

2. A video-signal processing apparatus as set forth in claim 1 further comprising: a manual input device for inputting variable character-code data to said character-information signal producing a device, whereby a variable optional character-information signal is produced by said character-information signal producing device.

3. A video-signal processing apparatus as set forth in claim 2, wherein said manual input device comprises a keyboard.

4. A video-signal processing apparatus as set forth in claim 1 further comprising respective isolation couplers for inputting the video signal and the control signal from the electronic endoscope to said apparatus and for electrically isolating the electronic endoscope from said apparatus.

5. A video-signal processing apparatus as set forth in claim 4, wherein each of said isolation couplers is a photo-coupler.

6. A video-signal processing apparatus as set forth in claim 4, wherein each of said isolation couplers is a transformer coupler.

7. A video-signal processing apparatus connectable to an electronic endoscope designed to output at least one kind of electric analog video signal, said apparatus comprising:

a character-information signal producing device that produces a character-information signal on the basis of character-code data;

an adder for adding the character-information signal to the electric analog video signal output from the electronic endoscope;

an analog-to-digital converter for converting the electric analog video signal carrying the character-information signal into a parallel electric digital video signal;

a parallel-to-serial converter for converting the parallel electric digital video signal into a serial electric digital video signal; and an output device from which the electric analog video signal output from the electronic endoscope and carrying the character-information signal is fed outside from said apparatus as the serial electric digital video signal.

8. A video-signal processing apparatus as set forth in claim 7, further comprising: a manual input device for inputting character-code data to said character-information signal producing device, whereby a variable optional character-information signal is produced by said character-information signal producing device.

9. A video-signal processing apparatus as set forth in claim 8, wherein said manual input device comprises a keyboard.

10. A video-signal processing apparatus as set forth in claim 7, further comprising an isolation coupler for inputting the video signal from the electronic endoscope to said apparatus, and for electrically isolating the electronic endoscope from said apparatus.

11. A video-signal processing apparatus as set forth in claim 10, wherein said isolation coupler is a photo-coupler.

12. A video-signal processing apparatus as set forth in claim 10, wherein said isolation coupler is a transformer coupler.

13. A video-signal processing apparatus as set forth in claim 7, further comprising an electrical-optical converter for converting the serial electric digital video signal into a serial optical digital video signal.

14. A video-signal processing apparatus as set forth in claim 7, further comprising a manual switch for forcibly stopping the feeding of the serial electric digital video signal from said apparatus.

15. A video-signal processing apparatus connectable to an electronic endoscope designed to output at least one kind of electric analog video signal, the electronic endoscope further outputting a control signal in response to a turning-ON of a function switch thereof, said apparatus comprising:

a memory for storing fixed character-code data;

a memory-reading device that reads the fixed character-code data from said memory in response to the control signal output from the electronic endoscope;

a character-information signal producing device that produces a fixed character-information signal on the basis of the fixed character-code data read from said memory;

an adder for adding the character-information signal to the electric analog video signal outputted from the electronic endoscope;

an analog-to-digital converter for converting the electric analog video signal carrying the character-information signal into a parallel electric digital video signal;

a parallel-to-serial converter for converting the parallel electric digital video signal into a serial electric digital video signal; and an output device from which the electric analog video signal output from the electronic endoscope and carrying the character-information signal is fed from said device as the serial electric digital video signal.

16. A video-signal processing apparatus as set forth in claim 15, further comprising: a manual input device for inputting variable character-code data to said character-information signal producing device, whereby a variable character-information signal is produced by said character-information signal producing device.

17. A video-signal processing apparatus as set forth in claim 16, wherein said manual input device comprises a keyboard.

18. A video-signal processing apparatus as set forth in claim 15, further comprising respective isolation couplers for inputting the video signal and the control signal from the electronic endoscope to said apparatus and for electrically isolating the electronic endoscope from said device.

19. A video-signal processing apparatus as set forth in claim 18, wherein each of said isolation couplers is a photo-coupler.

20. A video-signal processing apparatus as set forth in claim 18, wherein each of said isolation couplers is a transformer coupler.

21. A video-signal processing apparatus as set forth in claim 15, further comprising an electrical-optical converter for converting the serial electric digital video signal into a serial optical digital video signal.

22. A video-signal processing apparatus as set forth in claim 15, further comprising a manual switch for forcibly stopping the feeding of the serial electric digital video signal from said apparatus.

23. A video-signal processing apparatus connectable to an electronic endoscope designed to output a component-type electric analog color video signal as at least one kind of video signal, the component-type electric analog color video signal comprising a composite synchronizing signal-component and at least three kinds of video signal-components, said apparatus comprising:

a character-information signal producing device that produces a character-information signal on the basis of character-code data;

an adder for adding the character-information signal to the video signal-components;

an analog-to-digital converter for converting each of the respective video signal-components carrying the character-information signals into a parallel electric digital video signal-components;

a parallel-to-serial converter for converting the respective parallel digital video signal-components into serial digital video-signal-components and for outputting the serial digital video-signal-components in accordance with a series of clock pulses;

a phase-locked loop circuit for making a phase of said series of clock pulses coincide with a phase of the composite synchronizing signal component of the component-type electric analog color video signal; and an output device from which the serial digital video signal-components are output at proper timing from said apparatus.

24. A video-signal processing apparatus as set forth in claim 23, further comprising: a manual input device for inputting character-code data to said character-information signal producer, whereby a variable optional character-information signal is produced by said character-information signal producer.

25. A video-signal processing apparatus as set forth in claim 24, wherein said manual input device comprises a keyboard.

26. A video-signal processing apparatus as set forth in claim 23, further comprising an isolation coupler for inputting the video signal from the electronic endoscope to said apparatus and for electrically isolating the electronic endoscope from said apparatus.

27. A video-signal processing apparatus as set forth in claim 23, further comprising an electrical-optical converter for converting the serial electric digital video signal into a serial optical digital video signal.

28. A video-signal processing apparatus as set forth in claim 23, further comprising a manual switch for forcibly stopping the feeding of the serial electric digital video signal from said apparatus.

29. A video-signal processing apparatus as set forth in claim 23, further comprising:

a phase-lock detector for detecting the coincidence of the phase of the series of clock pulses and the phase of the composite synchronizing signal; and a signal-output stopping device that stops the output of the serial digital video-signal-components from said apparatus until said phase-lock detector detects the coincidence of the phase of the series of clock pulses with the phase of the composite synchronizing signal.

30. A video-signal processing apparatus as set forth in claim 29, further comprising a display for displaying a message announcing that the coincidence of the phase of the series of clock pulses with the phase of the composite synchronizing signal of the component-type electric analog color video signal is detected by said phase-lock detector.

31. A video-signal processing apparatus connectable to an electronic endoscope designed to output a component-type electric analog color video signal as at least one kind of video signal, the component-type electric analog color video signal comprising a composite synchronizing signal-component and at least three kinds of video signal-components, the electronic endoscope further outputting a control signal in response to a turning-ON of a function switch, said apparatus comprising:

a memory for storing fixed character-code data;

a memory-reading device that reads the fixed character-code data from said memory in response to the control signal output from the electronic endoscope;

a character-information signal producing device that produces a fixed character-information signal on the basis of the fixed character-code data read from said memory;

an adder for adding the character-information signal to the video signal-components;

an analog-to-digital converter for converting each of the respective video signal-components carrying the character-information signals into a parallel electric digital video signal-components;

a parallel-to-serial converter for converting the respective parallel digital video signal-components into serial digital video-signal-components and for outputting the serial digital video-signal-components in accordance with a series of clock pulses;

a phase-locked loop circuit for making a phase of said series of clock pulses coincide with a phase of the composite synchronizing signal component of the component-type electric analog color video signal; and an output device from which the serial digital video signal-components are output at proper timing from said apparatus.

32. A video-signal processing apparatus as set forth in claim 31, further comprising: a manual input device for inputting variable character-code data to said character-information signal producer, whereby a variable character-information signal is produced by said character-information signal producing device.

33. A video-signal processing apparatus as set forth in claim 32, wherein said manual input device comprises a keyboard.

34. A video-signal processing apparatus as set forth in claim 31, further comprising respective isolation couplers for inputting the video signal and the control signal from the electronic endoscope to said device and for electrically isolating the electronic endoscope from said apparatus.

35. A video-signal processing apparatus as set forth in claim 31, further comprising an electrical-optical converter for converting the serial electric digital video signal into a serial optical digital video signal.

36. A video-signal processing apparatus as set forth in claim 31, further comprising a manual switch for forcibly stopping the feeding of the serial electric digital video signal from said apparatus.

37. A video-signal processing apparatus as set forth in claim 31, further comprising:

a phase-lock detector for detecting the coincidence of the phase of the series of clock pulses with the phase of the composite synchronizing signal; and a signal-output stopping device that stops the output of the serial digital video-signal-components from said apparatus until said phase-lock detector detects the coincidence of the phase of the series of clock pulses with the phase of the composite synchronizing signal.

38. A video-signal processing apparatus as set forth in claim 31, further comprising a display for displaying a message announcing that the coincidence of the phase of the series of clock pulses with the phase of the composite synchronizing signal of the component-type electric analog color video signal is detected by said phase-lock detector.

39. A video-signal processing apparatus connectable to an electronic endoscope designed to output a component-type electric analog color video signal as at least one kind of video signal, the component-type electric analog color video signal comprising a composite synchronizing signal-component, a red video-signal-component, a green video-signal-component, and a blue video-signal-component, said apparatus comprising:

a color-conversion analog matrix circuit for producing a luminance signal-component, and two kinds of color-difference signal-components on the basis of the red, green, and blue video-signal-components;

a character-information signal producing device that produces a character-information signal on the basis of character-code data;

an adder for adding the character-information signal to each of the luminance signal-component and two kinds of color-difference signal-components;

an analog-to-digital converter for converting each of the respective luminance signal-component and two kinds of color-difference signal-components carrying the character-information signals into a parallel electric digital video signal-components;

a parallel-to-serial converter for converting the respective parallel digital video signal-components into serial digital video-signal-components and for outputting the serial digital video-signal-components in accodance with a series of clock pulses;

a phase-locked loop circuit for making a phase of said series of clock pulses coincide with a phase of the composite synchronizing signal component of the component-type electric analog color video signal; and an output device from which the serial digital video signal-components are output at proper timing from said apparatus.

40. A video-signal processing apparatus connectable to an electronic endoscope designed to output a component-type electric analog color video signal as at least one kind of video signal, the component-type electric analog color video signal comprising a composite synchronizing signal-component, a red video-signal-component, a green video-signal-component, and a blue video-signal-component, the electronic endoscope further outputting a control signal in response to a turning-ON of a function switch, said apparatus comprising:

a color-conversion analog matrix circuit for producing a luminance signal-component and two kinds of color-difference signal-components on the basis of the red, green, and blue video-signal-components;

a memory for storing fixed character-code data;

a memory-reading device that reads the fixed character-code data from said memory in response to the control signal outputted from the electronic endoscope;

a character-information signal producing device that produces a fixed character-information signal on the basis of the fixed character-code data read from said memory;

an adder for adding the character-information signal to each of the luminance signal-component and two kinds of color-difference signal-components;

an analog-to-digital converter for converting each of the respective luminance signal-component and two kinds of color-difference signal-components carrying the character-information signals into a parallel electric digital video signal-components;

a parallel-to-serial converter for converting the respective parallel digital video signal-components into serial digital video-signal-components and for outputting the serial digital video-signal-components in accordance with a series of clock pulses;

a phase-locked loop circuit for making a phase of said series of clock pulses coincide with a phase of the composite synchronizing signal component of the component-type electric analog color video signal; and an output device from which the serial digital video signal-components are output at proper timing from said apparatus.

41. A video-signal processing apparatus connectable to an electronic endoscope designed to output a component-type electric analog color video signal as at least one kind of video signal, the component-type electric analog color video signal comprising a composite synchronizing signal-component, a red video-signal-component, a green video-signal-component, and a blue video-signal-component, said apparatus comprising:

an analog-to-digital converter for converting each of the red, green, and blue video-signal-components into a parallel electric digital color video signal components;

a color-conversion digital matrix circuit for producing a parallel digital luminance signal-component, and two kinds of parallel digital color-difference signal-components on the basis of the parallel electric digital color video-signal-components;

a character-information signal producing device that produces a digital character-information signal on the basis of character-code data;

a digital adder for adding the digital character-information signal to each of the parallel digital luminance signal-component and two kinds of parallel digital color-difference signal-components;

an parallel-to-serial converter for converting the respective parallel digital luminance signal component and two kinds of parallel digital color-difference signal-components into serial digital video-signal-components and for outputting the serial digital video-signal-components in accordance with a series of clock pulses;

a phase-locked loop circuit for making a phase of said series of clock pulses coincide with a phase of the composite synchronizing signal component of the component-type electric analog color video signal; and an output device from which the serial digital video signal-components are output at proper timing from said apparatus.

42. A video-signal processing apparatus connectable to an electronic endoscope designed to output a component-type electric analog color video signal as at least one kind of video signal, the component-type electric analog color video signal comprising a composite synchronizing signal-component, a red video-signal-component, a green video-signal-component, and a blue video-signal-component, the electronic endoscope further outputting a control signal in response to a turning-ON of a function switch, said apparatus comprising:

an analog-to-digital converter for converting each of the red, green, and blue video-signal-components into a parallel electric digital color video signal components;

a color-conversion digital matrix circuit for producing a parallel digital luminance signal-component, and two kinds of parallel digital color-difference signal-components on the basis of the parallel electric digital color video-signal-components;

a memory for storing fixed character-code data;

a memory-reading device that reads the fixed character-code data from said memory in response to the control signal outputted from the electronic endoscope;

a character-information signal producing device that produces a digital character-information signal on the basis of character-code data;

a digital adder for adding the digital character-information signal to each of the parallel digital luminance signal-component and the two kinds of parallel digital color-difference signal-components;

a parallel-to-serial converter for converting the respective parallel digital luminance signal component and two kinds of parallel digital color-difference signal-components into serial digital video-signal-components and for outputting the serial digital video-signal-components in accordance with a series of clock pulses;

a phase-locked loop circuit for making a phase of said series of clock pulses coincide with a phase of the composite synchronizing signal component of the component-type electric analog color video signal; and an output device from which the serial digital video signal-components are output at proper timing from said apparatus.

43. A video-signal processing apparatus connectable to an electronic endoscope designed to output a component-type electric analog color video signal as at least one kind of video signal, the component-type electric analog color video signal comprising a composite synchronizing signal-component, a red video-signal-component, a green video-signal-component, and a blue video-signal-component, said apparatus comprising:

a color-conversion analog matrix circuit for producing a luminance signal-component, and two kinds of color-difference signal-components on the basis of the red, green, and blue video-signal-components;

an analog-to-digital converter for converting each of the luminance signal-component and two kinds of color-difference signal-components into a parallel electric digital video signal-components;

a character-information signal producing device that produces a digital character-information signal on the basis of character-code data;

a digital adder for adding the digital character-information signal to each of the parallel electric digital video signal-components;

a parallel-to-serial converter for converting the respective parallel electric digital video signal-components carrying the digital character-information signals into serial electric digital video-signal-components and for outputting the serial electric digital video-signal-components in accordance with a series of clock pulses;

a phase-locked loop circuit for making a phase of said series of clock pulses coincide with a phase of the composite synchronizing signal component of the component-type electric analog color video signal; and an output device from which the serial digital video signal-components are output at proper timing from said apparatus.

44. A video-signal processing apparatus connectable to an electronic endoscope designed to output a component-type electric analog color video signal as at least one kind of video signal, the component-type electric analog color video signal comprising a composite synchronizing signal-component, a red video-signal-component, a green video-signal-component, and a blue video-signal-component, the electronic endoscope further outputting a control signal in response to a turning-ON of a function switch, said apparatus comprising:

a color-conversion analog matrix circuit for producing a luminance signal-component, and two kinds of color-difference signal-components on the basis of the red, green, and blue video-signal-components;

an analog-to-digital converter for converting each of the respective luminance signal-component and two kinds of color-difference signal-components into a parallel electric digital video signal-components;

a memory for storing fixed character-code data;

a memory-reading device that reads the fixed character-code data from said memory in response to the control signal outputted from the electronic endoscope;

a character-information signal producing device that produces a fixed digital character-information signal on the basis of the fixed character-code data read from said memory;

a digital adder for adding the fixed digital character-information signal to each of the luminance signal-component and two kinds of color-difference signal-components;

a parallel-to-serial converter for converting the respective parallel digital video signal-components carrying the fixed digital character-information signal into serial electric digital video-signal-components and for outputting the serial electric digital video-signal-components in accordance with a series of clock pulses;

a phase-locked loop circuit for making a phase of said series of clock pulses coincide with a phase of the composite synchronizing signal component of the component-type electric analog color video signal; and an output device from which the serial electric digital video signal-components are output at proper timing from said apparatus.

45. A video-signal processing apparatus connectable to an electronic endoscope designed to output a component-type electric analog color video signal as at least one kind of video signal, the component-type electric analog color video signal comprising a composite synchronizing signal-component, a luminance signal-component, and two kinds of color-difference signal components, said apparatus comprising:

a character-information signal producing device that produces a character-information signal on the basis of character-code data;

an adder for adding the character-information signal to each of the luminance signal-component and two kinds of color-difference signal-components;

an analog-to-digital converter for converting each of the respective luminance signal-component and two kinds of color-difference signal-components carrying the character-information signals into a parallel electric digital video signal-components;

a parallel-to-serial converter for converting the respective parallel digital video signal-components into serial digital video-signal-components and for outputting the serial digital video-signal-components in accordance with a series of clock pulses;

a phase-locked loop circuit for making a phase of said series of clock pulses coincide with a phase of the composite synchronizing signal component of the component-type electric analog color video signal; and an output device from which the serial digital video signal-components are output at proper timing from said apparatus.

46. A video-signal processing apparatus connectable to an electronic endoscope designed to output a component-type electric analog color video signal as at least one kind of video signal, the component-type electric analog color video signal comprising a composite synchronizing signal-component, a luminance signal-component, and two kinds of color-difference signal components, the electronic endoscope further outputting a control signal in response to a turning-ON of a function switch, said apparatus comprising:

a memory for storing fixed character-code data;

a memory-reading device that reads the fixed character-code data from said memory in response to the control signal outputted from the electronic endoscope;

a character-information signal producing device that produces a fixed digital character-information signal on the basis of the fixed character-code data read from said memory;

an adder for adding the character-information signal to each of the luminance signal-component and two kinds of color-difference signal-components;

an analog-to-digital converter for converting each of the respective luminance signal-component and two kinds of color-difference signal-components carrying the character-information signals into parallel electric digital video signal-components;

a parallel-to-serial converter for converting the respective parallel digital video signal-components into serial digital video-signal-components and for outputting the serial digital video-signal-components in accordance with a series of clock pulses;

a phase-locked loop circuit for making a phase of said series of clock pulses coincide with a phase of the composite synchronizing signal component of the component-type electric analog color video signal; and an output device from which the serial electric digital video signal-components are output at proper timing from said apparatus.

47. A video-signal processing apparatus connectable to an electronic endoscope designed to output a component-type electric analog color video signal as at least one kind of video signal, the component-type electric analog color video signal comprising a composite synchronizing signal-component, a luminance signal-component, and two kinds of color-difference signal components, said apparatus comprising:

an analog-to-digital converter for converting each of the luminance signal-component and two kinds of color-difference signal-components into a parallel electric digital video signal-components;

a character-information signal producing device that produces a digital character-information signal on the basis of character-code data;

a digital adder for adding the digital character-information signal to each of the parallel electric digital video signal-components;

a parallel-to-serial converter for converting the respective parallel electric digital video signal-components carrying the digital character-information signals into serial electric digital video-signal-components and for outputting the serial electric digital video-signal-components in accordance with a series of clock pulses;

a phase-locked loop circuit for making a phase of said series of clock pulses coincide with a phase of the composite synchronizing signal component of the component-type electric analog color video signal; and an output device from which the serial electric digital video signal-components are output at proper timing from said apparatus.

48. A video-signal processing apparatus connectable to an electronic endoscope designed to output a component-type electric analog color video signal as at least one kind of video signal, the component-type electric analog color video signal comprising a composite synchronizing signal-component, a luminance signal-component, and two kinds of color-difference signal components, the electronic endoscope further outputting a control signal in response to a turning-ON of a function switch, said apparatus comprising:

an analog-to-digital converter for converting each of the respective luminance signal-component and two kinds of color-difference signal-components into a parallel electric digital video signal-components;

a memory for storing fixed character-code data;

a memory-reading device that reads the fixed character-code data from said memory in response to the control signal outputted from the electronic endoscope;

a character-information signal producing device that produces a fixed digital character-information signal on the basis of the fixed character-code data read from said memory;

a digital adder for adding the fixed digital character-information signal to each of the luminance signal-component and two kinds of color-difference signal-components;

a parallel-to-serial converter for converting the respective parallel digital video signal-components carrying the fixed digital character-information signal into serial electric digital video-signal-components and for outputting the serial electric digital video-signal-components in accordance with a series of clock pulses;

a phase-locked loop circuit for making a phase of said series of clock pulses coincide with a phase of the composite synchronizing signal component of the component-type electric analog color video signal; and an output device from which the serial electric digital video signal-components are output at proper timing from said apparatus.

49. A video-signal processing apparatus connectable to an electronic endoscope designed to output a component-type electric analog color video signal as at least one kind of video signal, the component-type electric analog color video signal comprising a composite synchronizing signal-component, and three kinds of video-signal-components, said apparatus comprising:

a synchronizing-signal detector for detecting an input composite synchronizing signal to said apparatus; and a signal-output stopping device that stops an output of the three kinds of video-signal-components from said device until said synchronizing-signal detector detects the input of the composite synchronizing signal to said apparatus.

50. A video-signal processing apparatus as set forth in claim 49, further comprising: a display for displaying a message announcing that said synchronizing-signal detector detects the input of the composite synchronizing signal to said apparatus.

51. A video-signal processing apparatus connectable to an electronic endoscope designed to output a component-type electric analog color video signal as at least one kind of video signal, the component-type electric analog color video signal comprising a composite synchronizing signal-component, and three kinds of video-signal-components, said apparatus comprising:

a converter/outputter for converting the three kinds of video-signal-components into serial digital video-signal-components and for outputting the serial digital video-signal-components outside from said apparatus in accordance with a series of clock pulses;

a phase-locked loop circuit for making a phase of said series of clock pulses coincide with a phase of the composite synchronizing signal component of the component-type electric analog color video signal;

a phase-lock detector for detecting the coincidence of the phase of the series of clock pulses with the phase of the composite synchronizing signal; and a signal-output stopping device that stops the output of the serial digital video-signal-components from said apparatus until said phase-lock detector detects the coincidence of the phase of the series of clock pulses with the phase of the composite synchronizing signal.

52. A video-signal processing apparatus as set forth in claim 51, further comprising a display for displaying a message announcing that the coincidence of the phase of the series of clock pulses with the phase of the composite synchronizing signal of the component-type electric analog color video signal is detected by said phase-lock detector.

53. A video-signal processing apparatus connectable to an electronic endoscope designed to output at least two kinds of video signals, said apparatus comprising:

a switch circuit provided in output-signal lines for the two kinds of video signals;

a first manual switch for forcibly stopping the output of one of the two kinds of video signals from said apparatus via said switch circuit when turning ON the first manual switch;

a first indicator associated with said first manual switch for indicating a turned-ON status of said first manual switch;

a second manual switch for forcibly stopping the output of a remaining one of the two kinds of video signals from said apparatus via said switch circuit when turning ON the second manual switch; and a second indicator associated with said second manual switch for indicating a turned-ON status of said second manual switch.

54. A video-signal processing apparatus as set forth in claim 53, wherein said one of the two kinds of video signals is a component-type analog color video signal composed of a composite synchronizing signal-component, and three kinds of video-signal-components; and said remaining one of said two kinds of video signal is an analog color S-video signal composed of a luminance signal-component and an amplitude-modulated color-difference signal-component.

55. A video-signal processing apparatus as set forth in claim 53, wherein said one of the two kinds of video signals is a component-type analog color video signal composed of a composite synchronizing signal-component, and three kinds of video-signal-components; and said remaining one of said two kinds of video signal is an analog color composite video signal combined with a luminance signal-component and an amplitude-modulated color-difference signal-component.

56. A video-signal processing apparatus as set forth in claim 53, wherein said one of the two kinds of video signals is an analog color S-video signal composed of a luminance signal-component and an amplitude-modulated color-difference signal-component; and said remaining one of said two kinds of video signal is an analog color composite video signal combined with a luminance signal-component and an amplitude-modulated color-difference signal-component.

* * * * *